(12) United States Patent
Schwab et al.

(10) Patent No.: US 11,439,372 B1
(45) Date of Patent: Sep. 13, 2022

(54) CUPLESS URINALYSIS STRIP HOLDER AND URINE COLLECTOR

(71) Applicant: UrynX, LLC, East Chatham, NY (US)

(72) Inventors: Brian Schwab, East Chatham, NY (US); Kenneth M. Kernen, Troy, MI (US)

(73) Assignee: UrynX LLC, East Chatham, NY (US)

( * ) Notice: Subject to any disclaimer, the term of this patent is extended or adjusted under 35 U.S.C. 154(b) by 0 days.

(21) Appl. No.: 17/406,020

(22) Filed: Aug. 18, 2021

Related U.S. Application Data

(63) Continuation-in-part of application No. 17/067,792, filed on Oct. 12, 2020, now Pat. No. 11,253,235.

(51) Int. Cl.
*A61B 10/00* (2006.01)

(52) U.S. Cl.
CPC ........ *A61B 10/007* (2013.01); *A61B 2505/07* (2013.01); *A61B 2560/04* (2013.01)

(58) Field of Classification Search
CPC .. A61B 10/0045; A61B 10/007; A61M 39/00; A61M 39/10; A61M 39/20; B01L 3/50; B01L 3/5021; B01L 3/5023; B01L 3/5029; B01L 3/5082
See application file for complete search history.

(56) References Cited

U.S. PATENT DOCUMENTS

| | | | |
|---|---|---|---|
| 2007/0166198 A1* | 7/2007 | Sangha | B01L 99/00 422/400 |
| 2015/0230872 A1* | 8/2015 | Lundkvist | A61B 10/0291 600/572 |

* cited by examiner

*Primary Examiner* — Daniel L Cerioni
*Assistant Examiner* — Raymond P Dulman
(74) *Attorney, Agent, or Firm* — Michael D. Eisenberg

(57) ABSTRACT

An aspect of some embodiment of the present invention relates to a kit for home urine collection and in office urine collection. The kit comprises a collector device and a clip. The collector device comprises a holder portion and a connector portion, the holder portion being configured to receive a sponge. The clip comprises an elongated main body and an extension extending perpendicularly to a longitudinal dimension of the main body, the extension being configured to cooperate with the holder portion to removably join the clip to the collector device.

9 Claims, 33 Drawing Sheets

A1

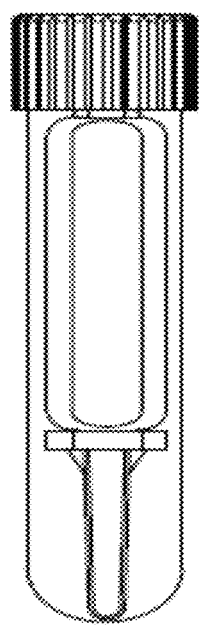
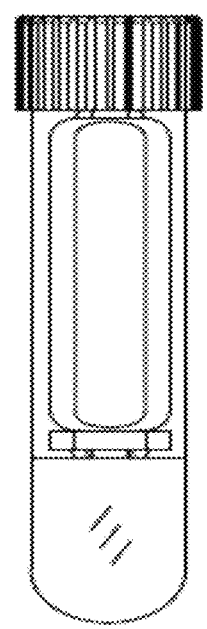
*FIG. 7A*  *FIG. 7B*
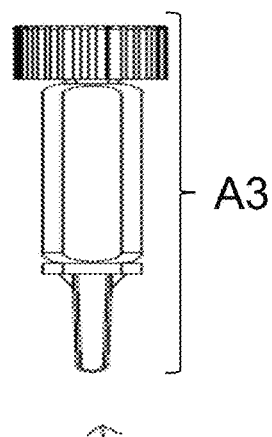
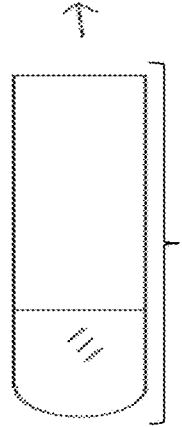
*FIG. 8*

CUPLESS URINALYSIS STRIP HOLDER AND URINE COLLECTOR

CROSS-REFERENCES TO RELATED APPLICATIONS

This application is a continuation in part of U.S. application Ser. No. 17/067,792 filed Oct. 12, 2020 and claims the benefit of U.S. Provisional Application Ser. No. 63/187,935 filed May 13, 2021, which is hereby incorporated herein by reference in their respective entirety.

BACKGROUND OF THE INVENTION

The spread of pandemics (COVID-19) and migration patterns where people are increasingly moving to exurban locations are factors which impose difficulties in obtaining biological samples or specimens for diagnostic testing. The contagiousness of COVID-19 has necessitated people to isolate from others. Diagnostic testing is needed which can use facilely obtained biological samples, while minimizing the risk of spreading pandemics (i.e., increasing safety when obtaining biological samples or specimens and efficiency for diagnostic testing). Exurban locations often lack the facilities for rapid, efficient, and safe diagnostic testing. Systems and methods are needed which enhance the efficiency of rapid and safe diagnostic testing for isolated populations. Additionally, in office procedures have also changed, with more scrutiny to lessen staff physical contact with patient and emphasis on streamlining all Specimen testing and collection.

SUMMARY OF THE EMBODIMENTS OF THE INVENTION

An aspect of some embodiment of the present invention relates to a kit for home urine collection and in office urine collection. The kit comprises a collector device and a clip. The collector device comprises a holder portion and a connector portion, the holder portion being configured to receive a sponge. The clip comprises an elongated main body and an extension extending perpendicularly to a longitudinal dimension of the main body, the extension being configured to cooperate with the holder portion to removably join the clip to the collector device.

In a variant, the kit includes a cap configured to cooperate with the connector portion to of the collector device, to join the cap and the collector device when the cap closes a tube in which the collector device is placed.

In some embodiments of the present invention, the connector portion comprises a lid and two flexible prongs extending upward from the top of the lid. The prongs are disposed so that a lower cavity and an upper cavity are located between the prongs and are connected to each other. The lower cavity has a circular side-cross section and is wider than the upper cavity.

In a variant, the extension is cylindrical and configured to be inserted in the lower cavity to join the clip to the collection device, such that clip is rotatable around the extension with respect to the collection device, when the clip is connected to the collection device.

In another variant, extension clears the connector portion of the collection device to enable rotation of 360 degrees of the clip around the extension with respect to the collection device, when the clip is connected to the collection device.

In yet another variant, the kit comprises a flange at or near an end of the extension that is farthest from the main body, wherein the flange is perpendicular to the extension and sized to pass through the upper cavity.

In a further variant, the main body has a planar shape and includes a front surface and a rear surface. The main body comprises an arm extending from a lateral side of the main body and sloping rearward of the rear surface. The arm comprises a tab that extends toward the rear surface and presses against the rear surface. The arm is movable rearward to open a gap between the tab and the rear surface for insertion of a test strip in the gap. When the arm is released, the arm is configured for closing the gap to hold the test strip between the tab and the rear surface.

In yet a further variant, the kit comprises a cap configured to cooperate with the connector portion to of the collector device, to join the cap and the collector device when the cap closes a tube in which the collector device is placed. The cap comprises a hollow cylindrical protrusion extending from a bottom surface of a top of the cap downward, the hollow cylindrical protrusion having an open bottom end. The hollow cylindrical protrusion comprises a lip extending radially inward between a top and a bottom end of the hollow cylindrical protrusion. The flexible prongs comprise grooves on outer sides thereof, such that the prongs are received in the hollow cylindrical protrusion of the cap when the cap closes the tube, and the grooves cooperate with the lip of the hollow cylindrical protrusion to connect the collection device to the cap.

In a variant, an inner portion of the hollow cylindrical protrusion widens from the top to the bottom end of the hollow cylindrical protrusion.

In some embodiments of the present invention, the longitudinal dimension of the main body is substantially equal to a longitudinal dimension of the collector device.

Another aspect of some embodiments of the present invention relates to a kit for home urine collection and in office urine collection. The kit comprises a sponge, a collector device, a clip, a tube, a cap, a test strip. The sponge is configured for absorbing urine when urinated upon. The collector device comprises a holder portion and a connector portion, the holder portion being configured to receive the sponge. The clip comprises an elongated main body and an extension extending perpendicularly to a longitudinal dimension of the main body, the extension being configured to cooperate with the holder portion to removably join the clip to the collector device. The tube is configured to receive the collector device. The cap configured to cooperate with the connector portion to of the collector device, to join the cap and the collector device when the cap closes the tube in which the collector device is placed. The test strip comprises distinct chemical pads with respective reagents that change color upon physical exposure to urine depending on presence of entities in the urine. The main body has a planar shape and includes a front surface and a rear surface. The main body comprises an arm extending from a lateral side of the main body and sloping rearward of the rear surface. The arm comprises a tab that extends toward the rear surface and presses against the rear surface. The arm is movable rearward to open a gap between the tab and the rear surface for insertion of the test strip in the gap. When the arm is released, the arm is configured for closing the gap to hold the test strip between the tab and the rear surface.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 7A is a depiction of the urine collection device in a sealed tube.

FIG. 7B is a depiction of urine extracted from the urine collection device in the sealed tube.

FIG. 8 is a depiction of a mechanism for removing the urine collection device from the sealed tube.

FIG. 25 illustrates a kit of the present invention, in which a test strip is joined to the clip.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Reference is also made to the figures, as presented herein. The figures are not intended to be exhaustive or to limit the invention to the precise form disclosed. It should be understood that the invention can be practiced with modification and alteration, and that the invention be limited only by the claims and the equivalents thereof.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The systems and methods herein are directed to a urine analysis kit for telemedicine systems and in-office settings The urine analysis kit comprises: one unit of a urine strip holder, two units of 10-parameter urine test strips in a foil packet or one strip attached to the device in a sterile packet, one unit of a urination device, one unit of a sterile zip-lock bag, and one unit of a sponge-mounted urine collection device.

The part number and corresponding description of the part are listed in Table 1.

TABLE 1

| Components which construct the Urine Collection Device | | | |
| --- | --- | --- | --- |
| Sponge Stopper 105 | Sponge Holder 110A, 110B, 110C, or 110D | Connector 115 | Side extenders 120 |
| Receiving Cavity 125 | Receiving Cavity 127 | Receiving Cavity 130 | Wall 135 |
| Seat 140 | Support Extenders 145 | Sponge 150A, 150B, 150C, or 150D | Clip 155 |
| Base 160 | Base 165 | Receiving Extender 170 | Receiving Extender 175 |
| Cap 180 | Extender 185 | Knob 190 | Support Extender 193 |
| Collection Device 195 (which comprises either sponge holder 110A, 110B, 110C, and 110D) | Clip 200 | Groove 205 | Groove 207 |
| Layer 209 Layer 213 Urinalysis Strip 351 | Layer 210 | Layer 211 | Layer 212 |

To facilitate understanding the systems and methods herein, the following assemblies are listed below.

Figure 1:
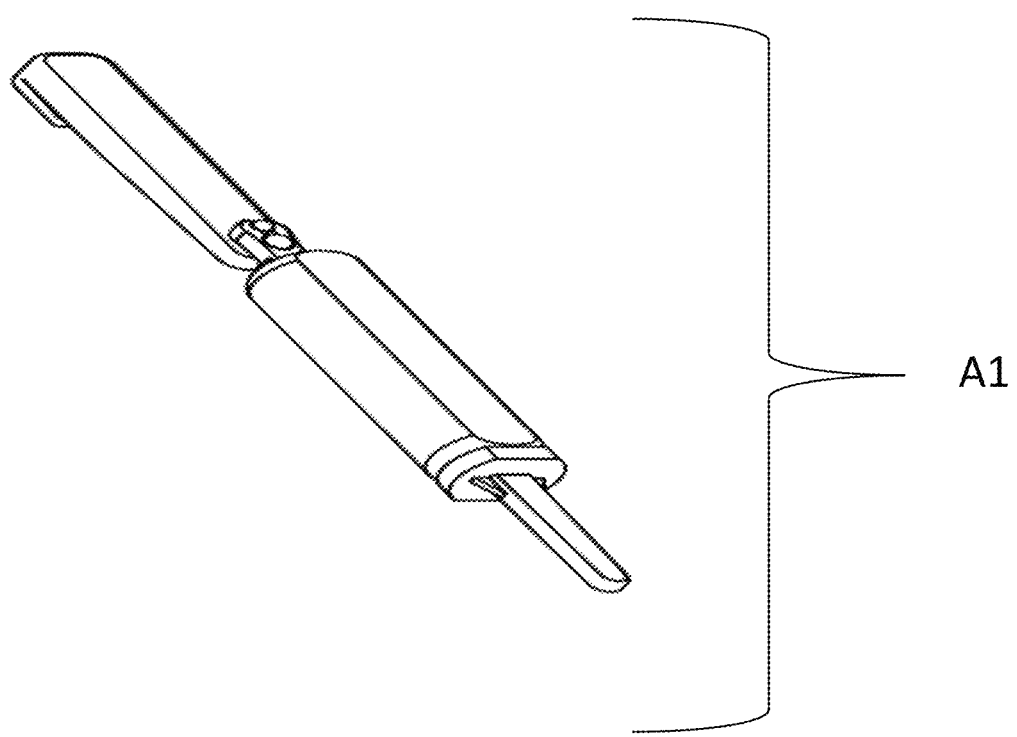
FIG. 1 is a depiction of a perspective view of the urine collection device attached with the rotatable clip.
Figure 2A:
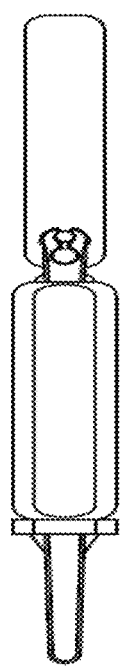
FIG. 2A, FIG. 2B, and FIG. 2 are depictions of a front view, back view, and side view of the urine collection device, respectively.
Figure 2B:
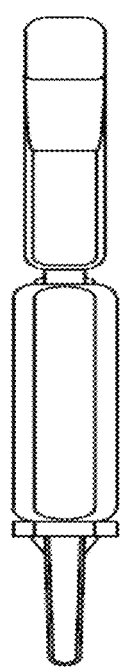
Figure 2C:
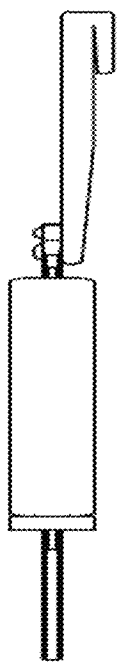
Figure 3:
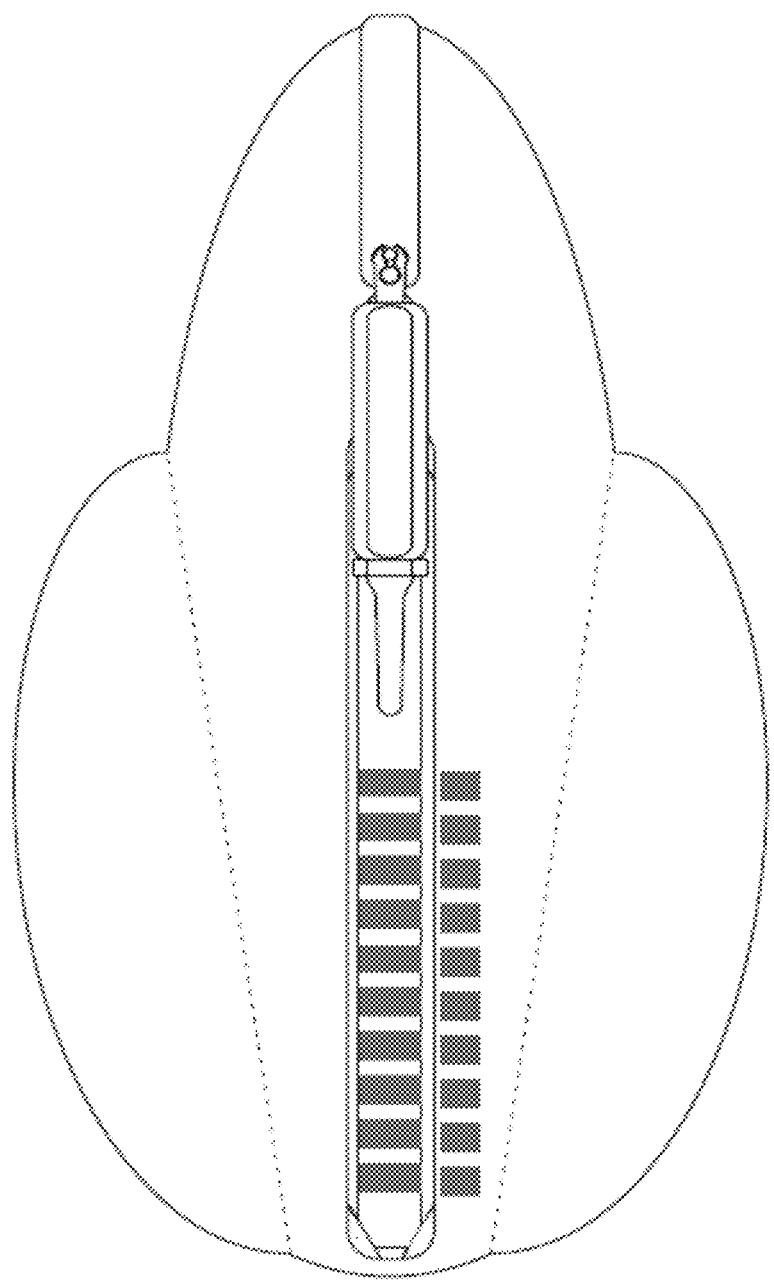
FIG. 3 is a depiction of the urine collection device attached to a strip holder.
Figures 4A, 4B:
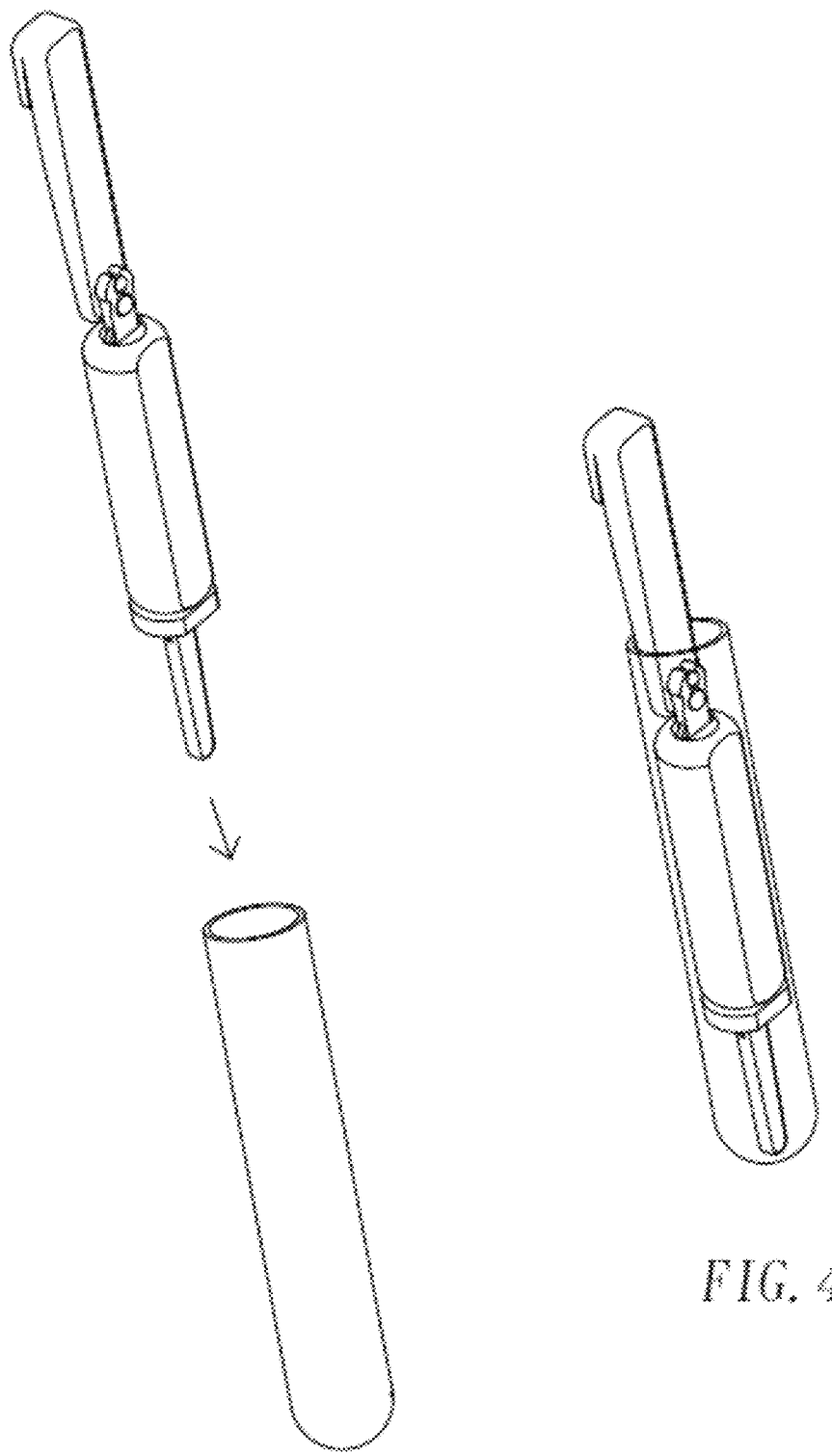
FIG. 4A and FIG. 4B are depictions of the urine collection device with a rotatable clip placed into a centrifuge tube.
Figures 5A, 5B:
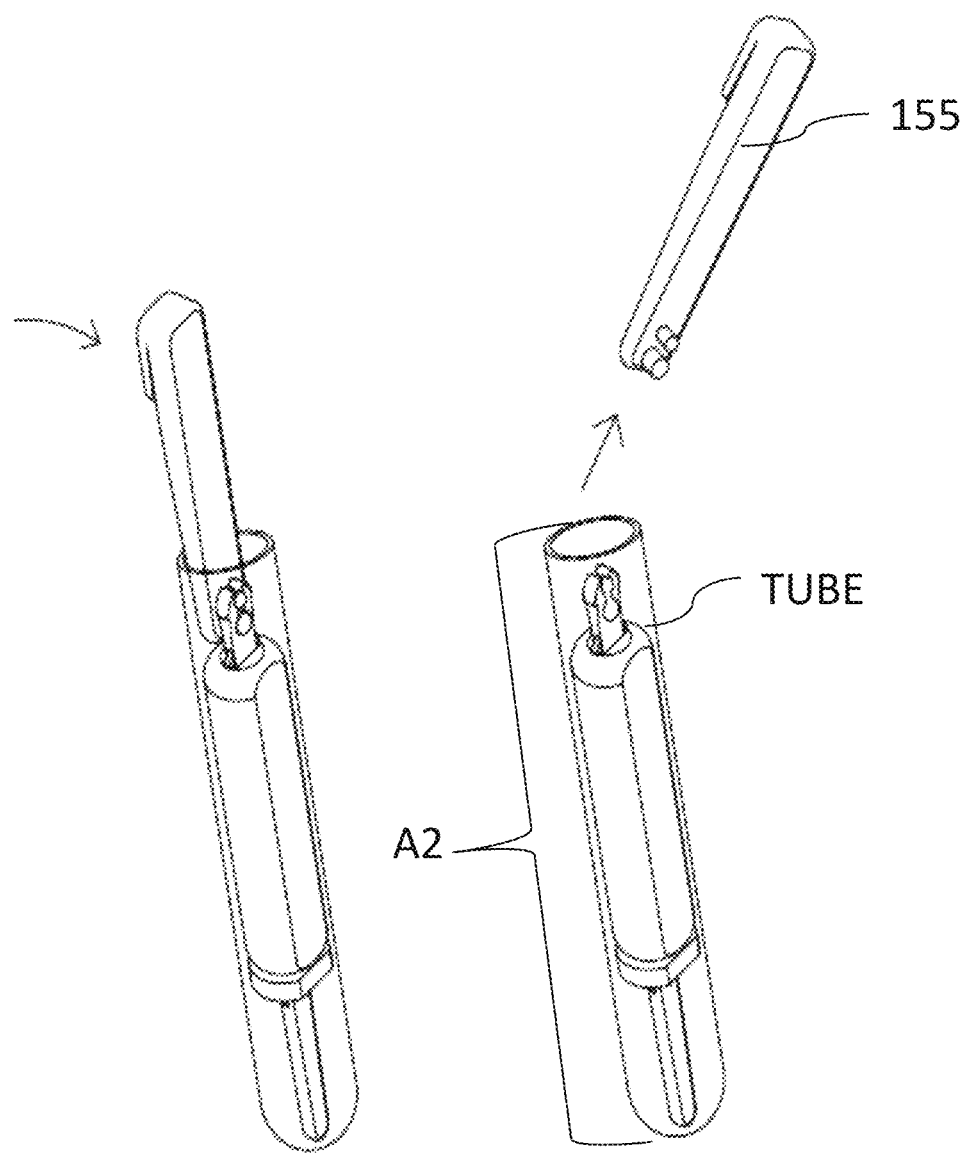
FIGS. 5A and 5B are depictions of a mechanism for removing the rotatable clip from the urine collection device.

Assembly 1 (A1) comprises collection device 195 operatively connected to clip 155. Sponge holder 110A is integrated into this variant of collection device 195, wherein sponge holder 110A receives sponge 150A. In FIG. 1, a perspective view of A1 is depicted. In FIG. 2A, a front view of A1 is depicted. In FIG. 2B, a rear view of A1 is depicted, which is a 180 degree rotation of FIG. 2A. In FIG. 2C, a side view of A1 is depicted, which is a 90 degree rotation of FIG. 2A. In FIG. 3, A1 is placed in contact with a urine analysis strip holder. Stated another way, collection device 195 may be attached to the urine analysis strip holder by clip 155. Thereby, the urine strip holder can be held together with collection device 195. The combination of the urine strip holder held together with collection device 195 can be handled by the user of collection device 195. For a user performing only urine specimen collection, the user can simply hold clip 155 and urinate on collection device 195 such that the sponge absorbs the urine. Thus, the urine strip holder is not necessary for collector device 195 to collect urine specimens. Within the urine analysis strip holder, a basic diagnostic tool for determining pathological changes in a patient's urine is placed, such as a urine test strip. The urine test strip comprises up to 10 distinct chemical pads (with reagents that change color upon physical exposure to urine). Color changes may indicate the presence (for example presence above a certain concentration) of ketones, proteins, acidic entities, and so forth in the urine. In FIG. 4A, A1 is detached from a tube. In FIG. 4B, A1 is inserted into the tube from FIG. 4A. In FIG. 5A, a user can detach clip 155 from A1 at the indicated position on clip 155.

Assembly 2 (A2) comprises collection device 195 operatively connected to sponge 150A. Sponge holder 110A is integrated into this variant of collection device 195, whereby clip 155 has been detached from the collection device 195. Sponge holder 110A receives sponge 150A. In FIG. 5B, clip 155 has been detached to yield A2 from A1, wherein A2 remains inserted into the tube.

Figures 6A, 6B:
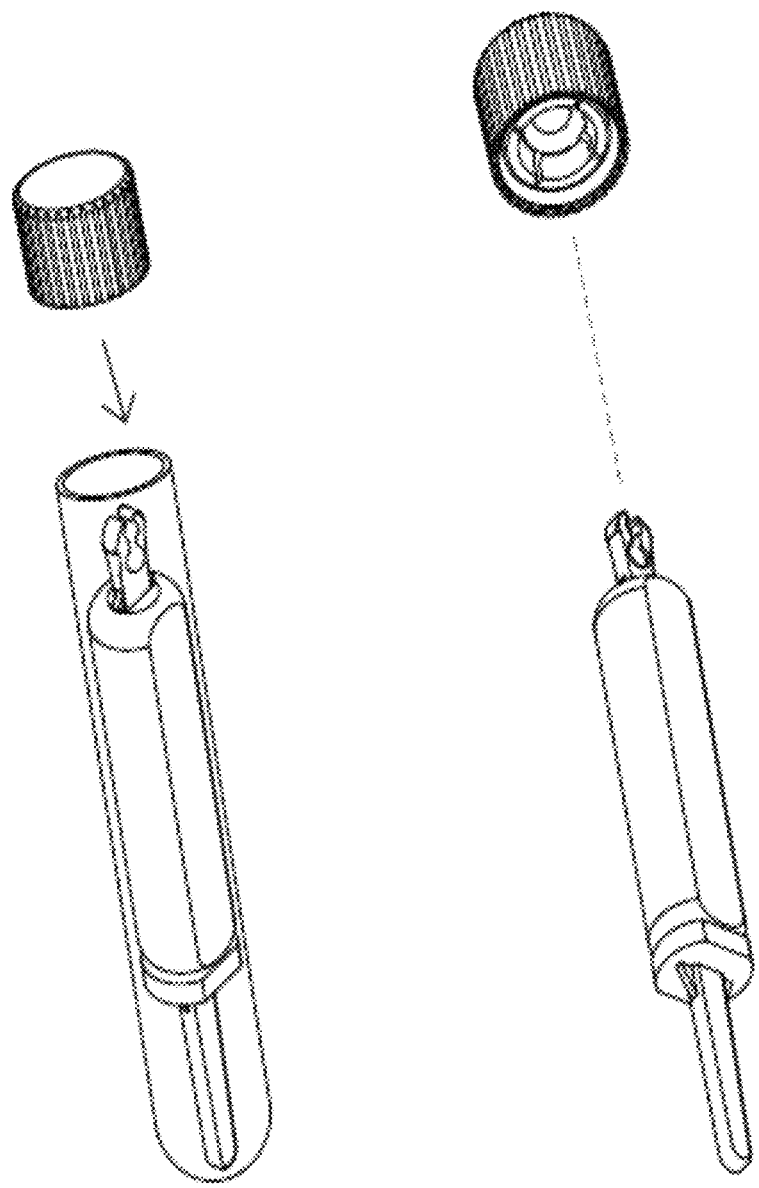
FIGS. 6A and 6B are depictions of a mechanism for connecting a cap to the urine collection device.
Figure 11:
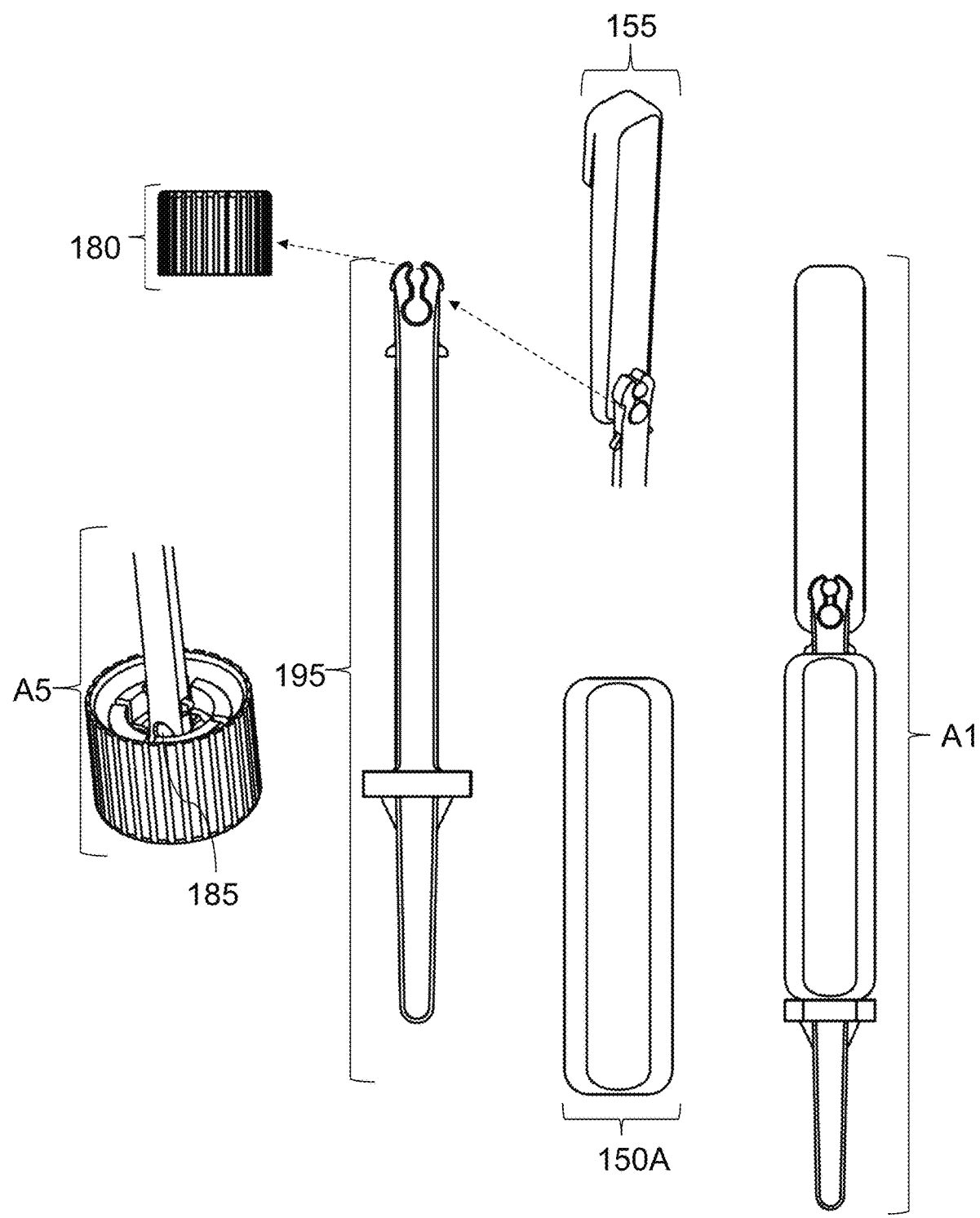
FIG. 11 is a depiction of mechanisms of attaching components to the urine collection device.

Assembly 3 (A3) comprises collection device 195 operatively connected to cap 180. Sponge holder 110A is integrated into this variant of collection device 195. Sponge holder 110A receives sponge 150A. In FIG. 6A, cap 180 comprises extender 185 (as depicted in FIG. 11) to receive collection device 195 which resides within the tube. In FIG. 6B, cap 180 comprises extender 185 (as depicted in FIG. 11) to receive collection device 195 which is outside of the tube. In FIG. 6A and FIG. 6B, cap 180 is about to be connected to collection device 195 of A2. In FIG. 7A, cap 180 is operatively connected to the tube and collection device 195 of A2, thereby forming a capped system containing the sponge (with collected urine). In FIG. 7B, the capped system can undergo centrifuge or other processes in which collected urine in the sponge migrates to the bottom of the tube.

Assembly 4 (A4) comprises the tube where urine from a sponge (sponge 150A, 150B, or 150C) has been: (i) collected in the tube and (ii) detached from A3, as depicted in FIG. 8. The connection of collector device 195, which is holding sponge 150A, to cap 180 is sturdy. By unscrewing cap 180 from the tube, A4 results without disturbing the urine in the bottom the tube. For example, 5 mL of urine migrates to the bottom of the tube, wherein the urine has been collected in the sponge.

Figure 9:
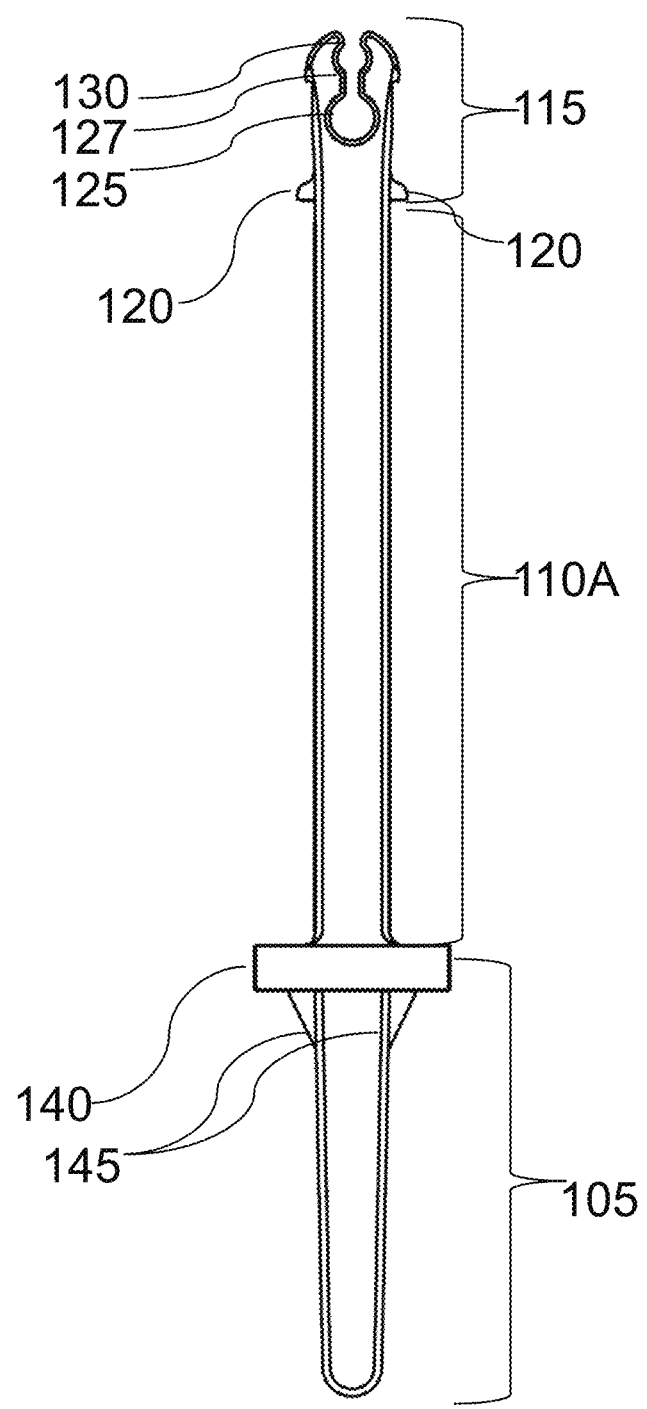
FIG. 9 is a depiction of components of the urine collection device.
Figure 10:
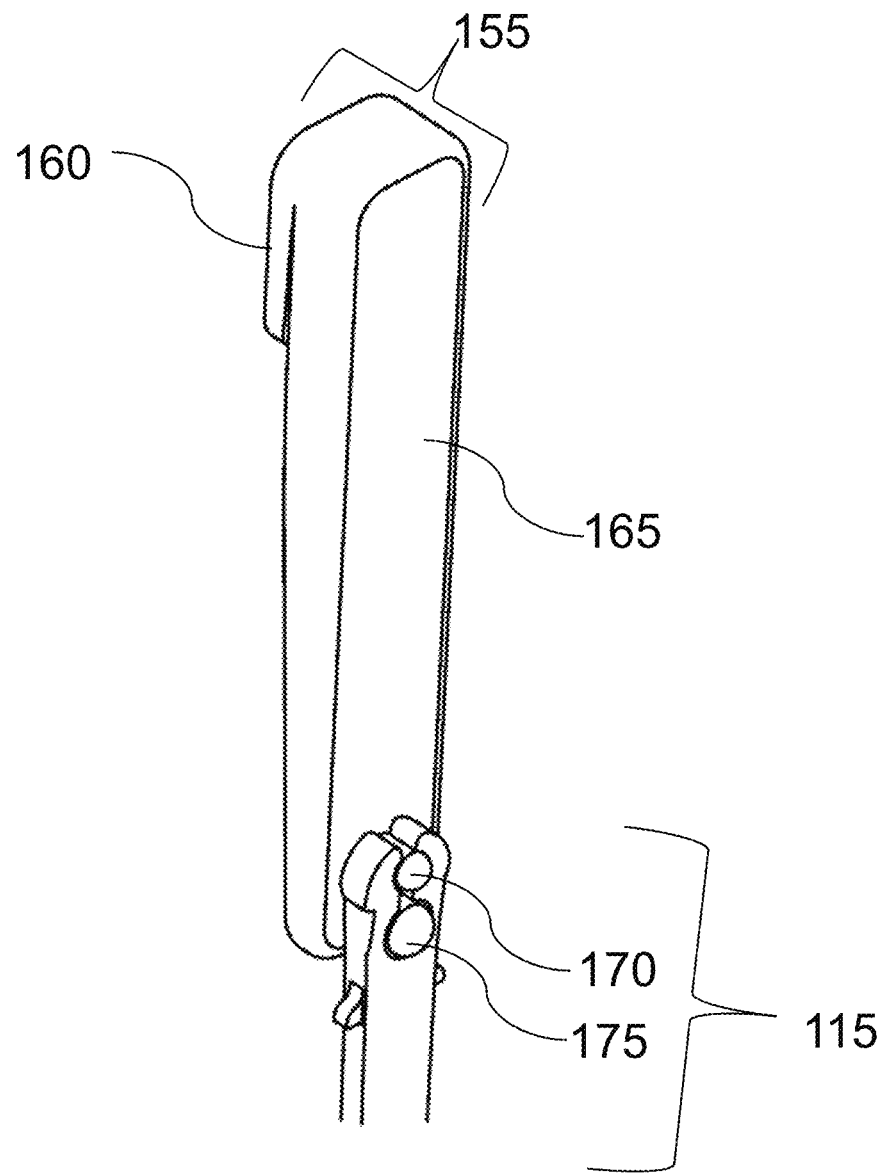
FIG. 10 is a depiction of components of the rotatable clip.
Figure 12:
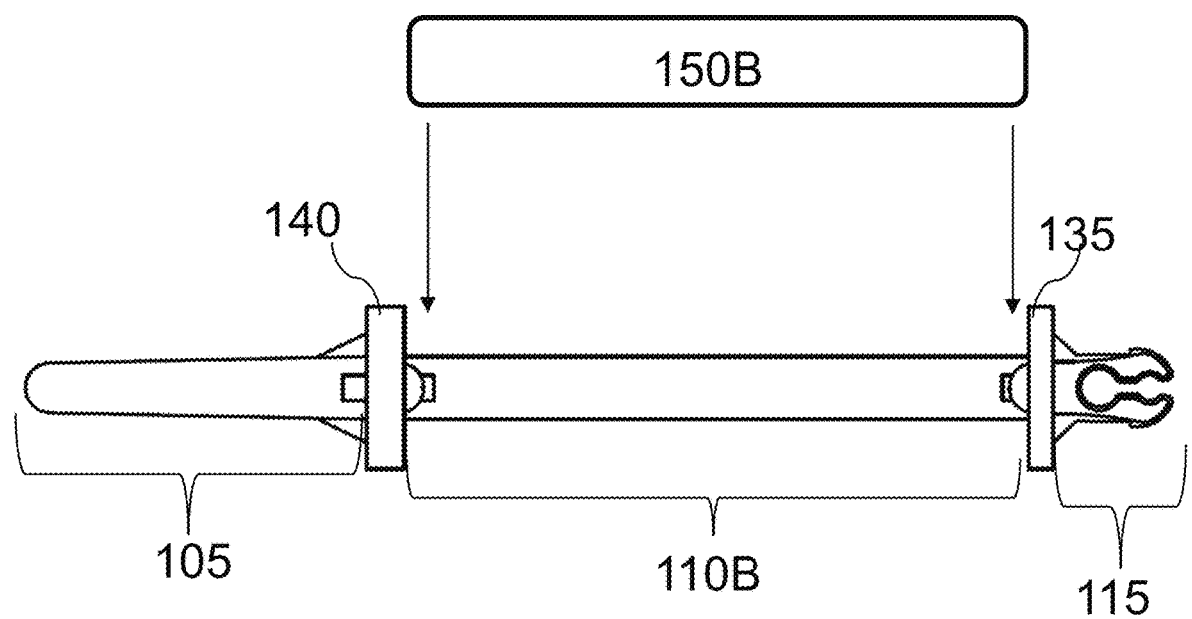
FIG. 12 is a depiction of top view of a urine collection device having a wall and a seat without knobs.
Figure 13:
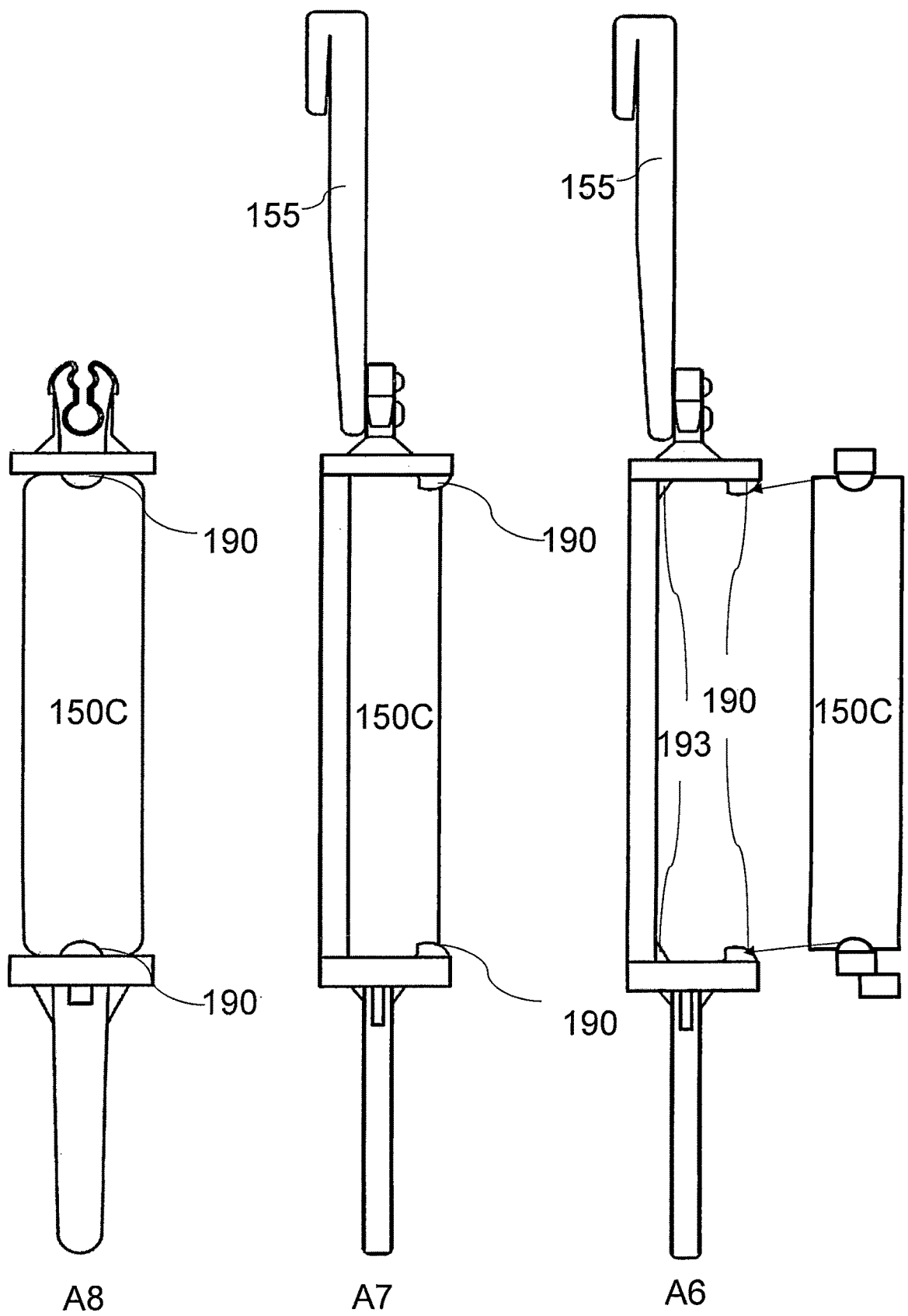
FIG. 13 is a depiction of a urine collection device having a wall and a seat with knobs.

The collector portion of sponge-mounted urine collection device (e.g. UriSponge™) is collection device 195, as depicted in FIG. 9. Collection device 195 can be attached to and detached from clip 155 at connector 115 of collection device 195, wherein connector 115 is operatively connected to sponge holder 110A or sponge holder 110B of collection device 195. Sponge holder 110A or 110B is operatively connected to sponge stopper 105 of collection device 195. Sponge stopper 105 is configured to contact a bottom surface of a tube and offset sponge holder 110A away from the bottom surface of the tube. Sponge holder 110A comprises side extenders 120 and seat 140, which are arranged such that sponge 150A (which has a concave groove) fits in between side extenders 120 and seat 140. In an embodiment, sponge holder 110B comprises wall 135 and seat 140, which are arranged such that sponge 150B fits in between wall 135 and seat 140. In another embodiment, sponge holder 110C comprises wall 135 and seat 140 such that there is at least one unit of knob 190 and rear extender 193 disposed on the surface of wall 135 and seat 140, as depicted in FIG. 13. In FIG. 12, sponge 150B is rectangular and fits within wall 135 and seat 140, which define the top and bottom boundaries of sponge holder 110B. In contrast, sponge 150C contains two grooves to fit within each unit of knob 190 and two grooves to fit with each unit of knob 193. In FIG. 13, Wall 135 and seat 140 are arranged such that sponge 150C fits in between wall 135 and seat 140, which each have a unit of knob 190 and rear extender 193 attached thereon. Rear extender 193 protrudes up and away from sponger holder 110B.

Assembly 5 (A5) comprises cap 180 operatively connected to collection device 195, as depicted in FIG. 11. sponge holder 110A is integrated into collection device 195. Stated another way, cap 180 is configured to receive connector 115 of collection device 195.

Assembly 6 (A6) comprises collection device 195 operatively connected to clip 155. Sponge holder 110B, which comprises two units of knob 190 and two units of rear extender 195, is integrated into this variant of collection device 195, wherein sponge holder 110B is configured to receive sponge 150C, as depicted in FIG. 13.

Assembly 7 (A7) comprises collection device 195 operatively connected to clip 155 and sponge 150C. Sponge holder 110B, which comprises two units of knob 190 and two units of rear extender 195, is integrated into this variant of collection device 195, wherein sponge holder 110B receives sponge 150C, as depicted in FIG. 13.

Figure 15:
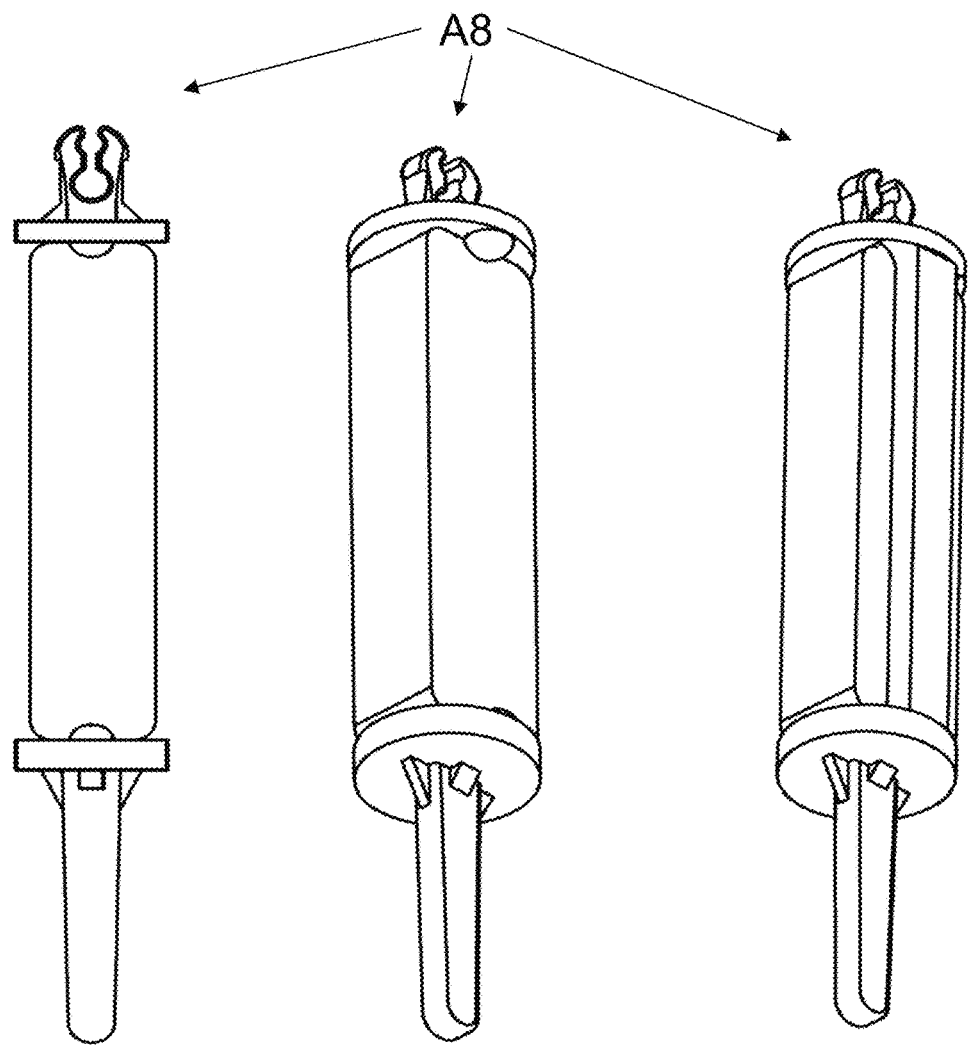
FIG. 15 is a depiction of the urine collection device having the wall and the seat with the knobs, where a sponge is disposed in between the wall and the seat and the cap is disconnected.

Assembly 8 (A8) comprises collection device 195 operatively connected to sponge 150C. Clip 155 has been detached from A7 to yield A8, as depicted in FIG. 13. Other views of A8 are depicted in FIG. 15.

Figure 14:
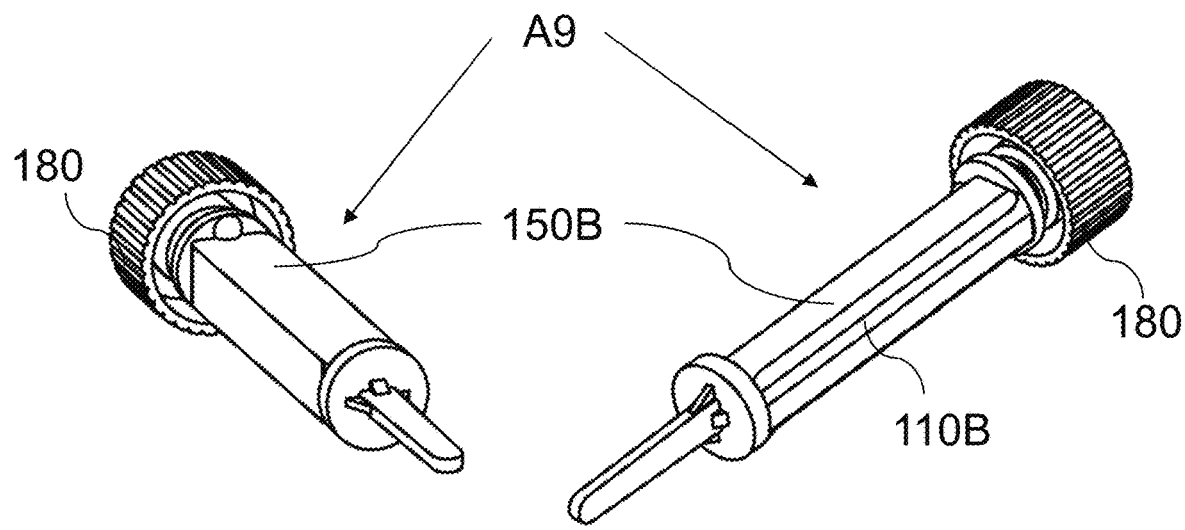
FIG. 14 is a depiction of the urine collection device having the wall and the seat with the knobs, where a sponge is disposed in between the wall and the seat and a cap is connected to the urine collection device.

Assembly 9 (A9) comprises collection device 195 operatively connected to sponge 150C and cap 180. Sponge holder 110B, which comprises two units of knob 190 and two units of rear extender 195, is integrated into this variant of collection device 195, wherein sponge holder 110B receives sponge 150C. Two different views of the A9 are depicted in FIG. 14.

Figure 16:
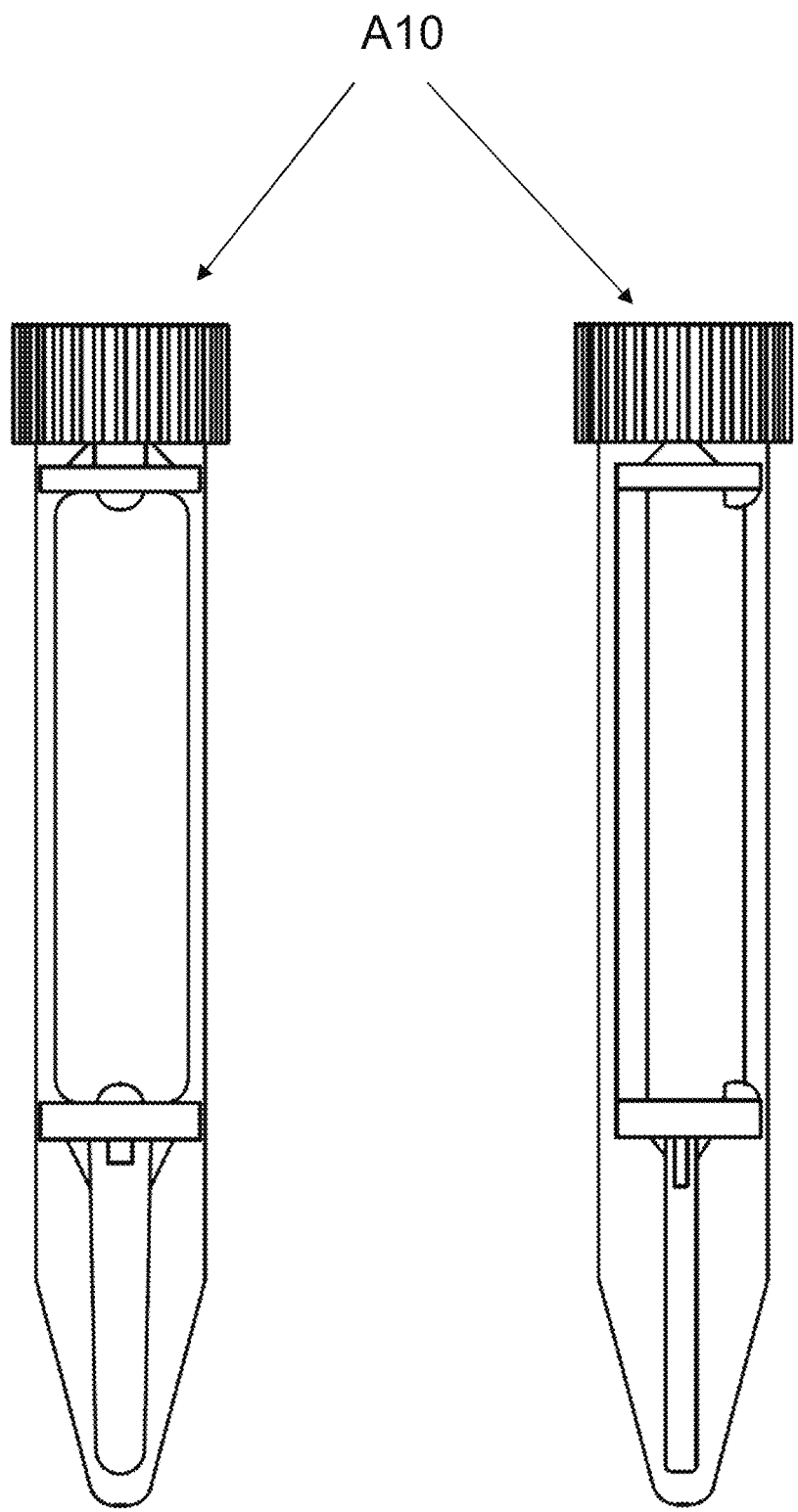
FIG. 16 is a depiction of the urine collection device having the wall and the seat with the knob, where a sponge is disposed in between the wall and the seat and the cap is connected to the urine collection device and tube for centrifuging.

Assembly 10 (A10) comprises collection device 195 operatively connected to sponge 150C, cap 180, and the tube (similar or identical to the tube described above). Sponge holder 110B, which comprises two units of knob 190 and two units of rear extender 195, is integrated into this variant of collection device 195, wherein sponge holder 110B receives sponge 150C, as depicted in FIG. 16. Cap 180 is operatively connected to collection device 195 via attachment of extender 185 of cap 180 with connector 115 of collection device 195. Connector 115 comprises receiving cavity 125, receiving cavity 127, and receiving cavity 130 to form sturdy connections with cap 185. Receiving cavity 130 and receiving cavity 127 have curve-shaped cavity regions which are connected by a straight-shaped receiving cavity 127. Clip 115 can also attach to receiving cavity 125, receiving cavity 127, and receiving cavity 130 of connector 115 to form sturdy connections and readily detach from receiving cavity 125, receiving cavity 127, and receiving cavity 130 of connector 115. The sturdy connections between connector 115 and clip 155 are formed upon receiving extender 170 operatively connecting to receiving cavity 130 and receiving extender 175 operatively connecting to receiving cavity 125. Clip 155 comprises base 165 and base 160, wherein base 165 and base 160 are fused together. Receiving extenders 170 and 175 are disposed on the bottom portion of base 165. Base 160 is disposed on the top portion of base 165. Base 160 protrudes outwards, whereby the user can apply a force against base 160 to detach clip 155 from A1, as depicted in FIG. 5A and FIG. 5B.

Figure 17A:
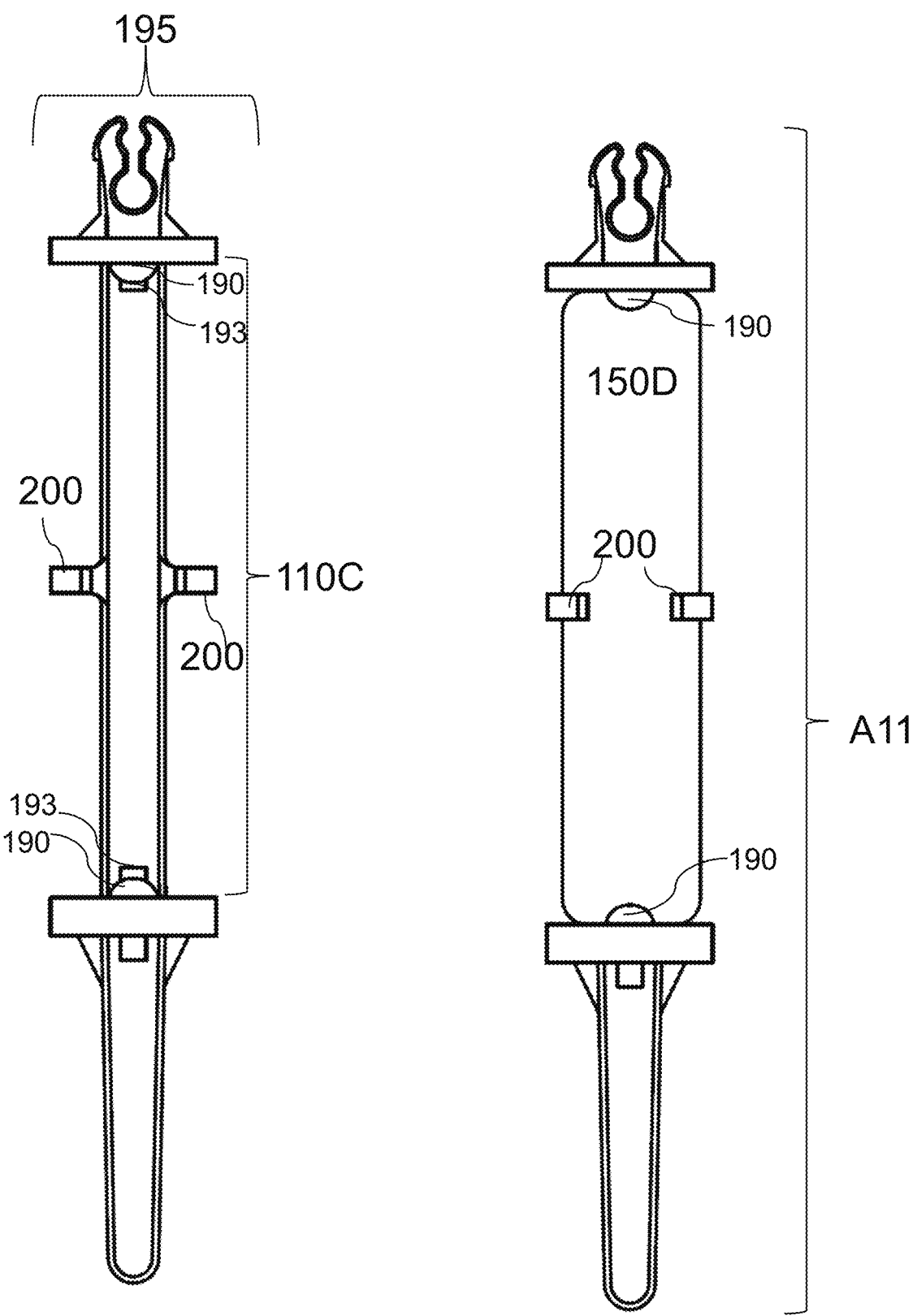
FIG. 17 is a depiction of the urine collection device having the wall and the seat with knobs and rotatable clips, where a sponge is disposed in between the wall and the seat and the cap is connected to the urine collection device and tube for centrifuging.
Figure 17B:
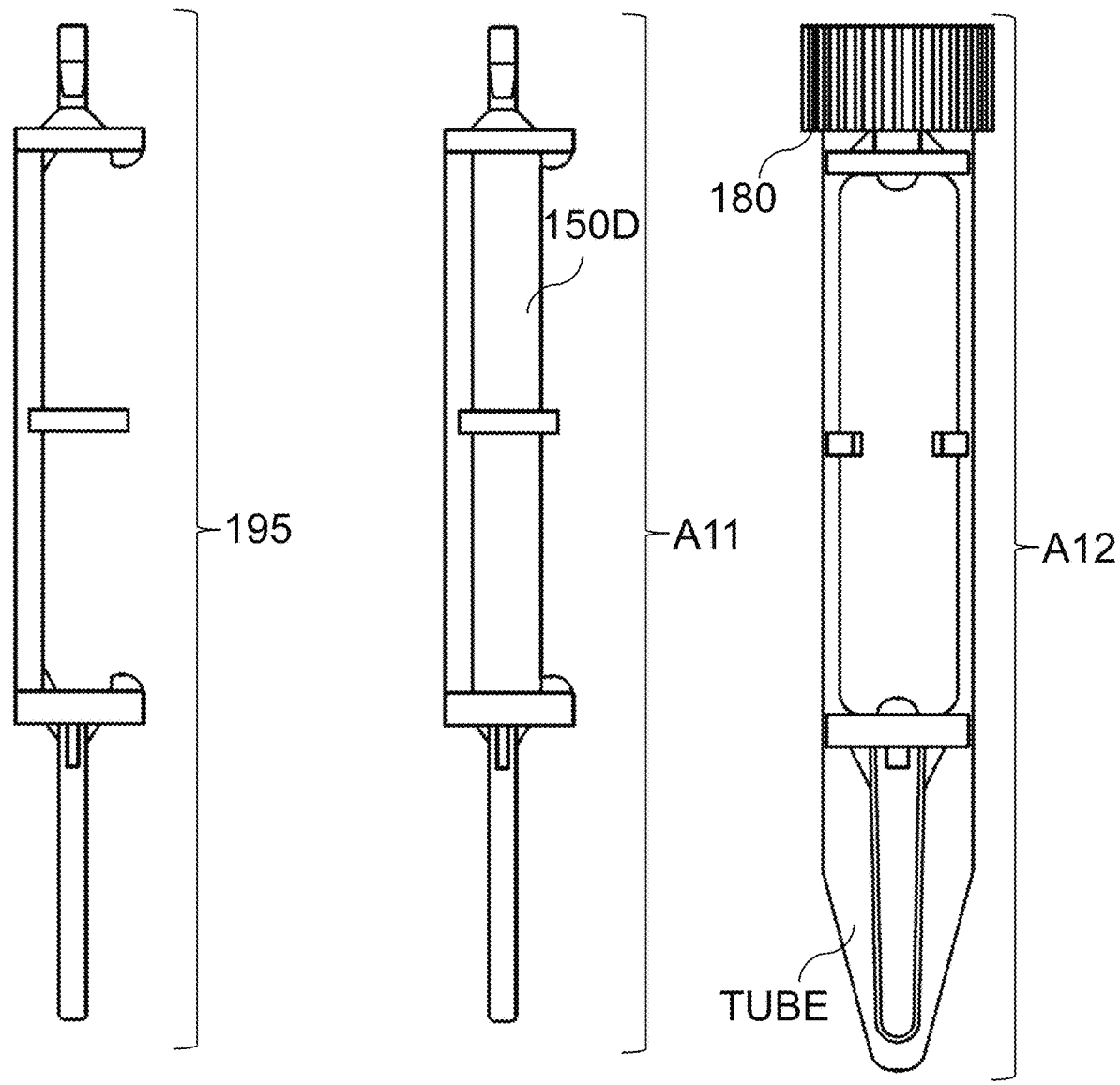
Figure 18:
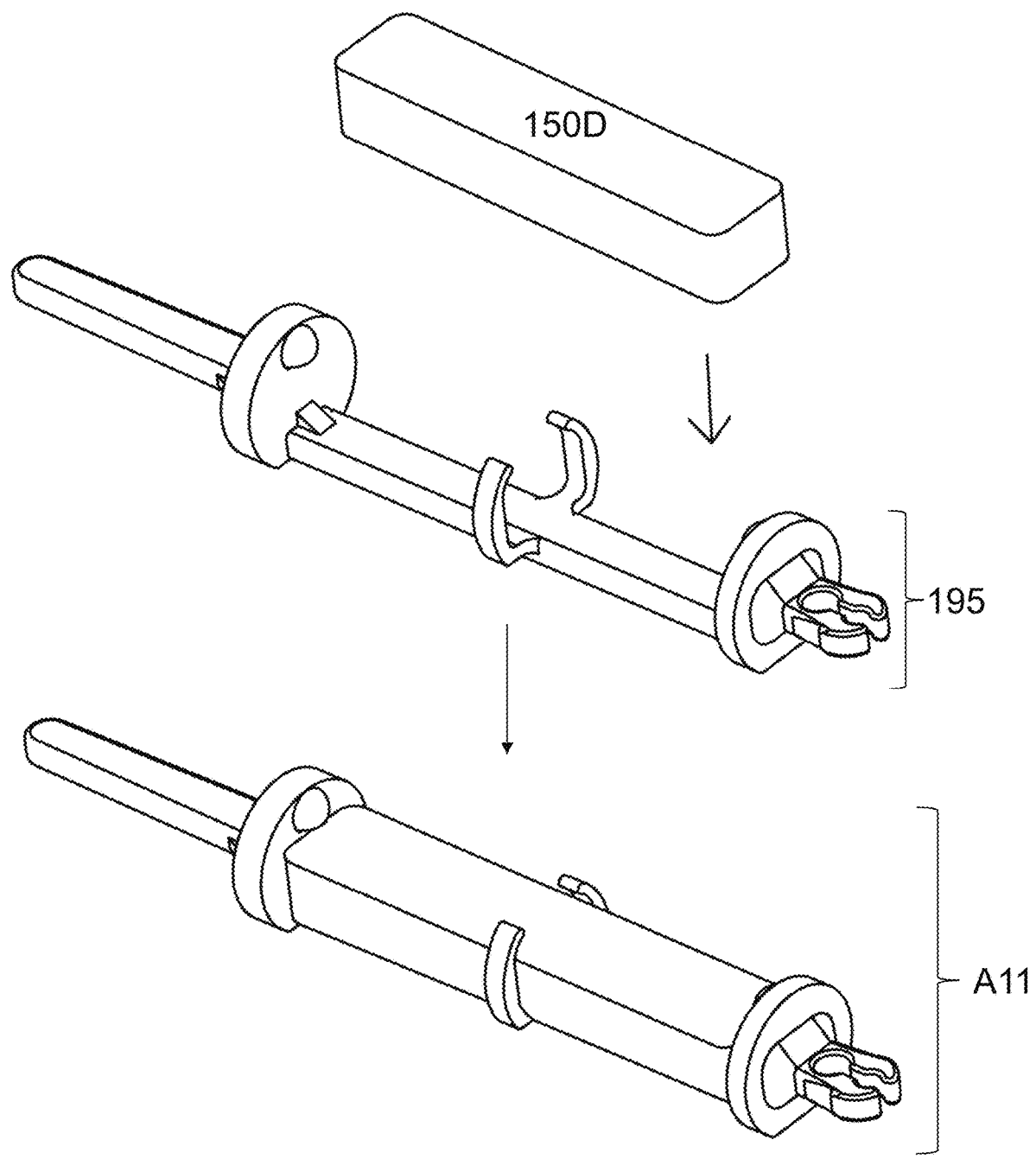
FIG. 18 is a depiction of a mechanism of attaching the sponge to the urine collection device having the wall and the seat with knobs and clips.

Assembly 11 (A11) comprises collection device 195 operatively connected to sponge 150D, as depicted in FIG. 17 and FIG. 18. Sponge 150D comprises straight line incisions in the body of the sponge, as depicted in FIG. 18. Sponge holder 110C, which comprises two units of knob 190, two units of rear extender 195, and two units of clips 200, is integrated into this variant of collection device 195, wherein sponge holder 110C receives sponge 150D, as depicted in FIG. 17. Sponge 150D makes a supple fit within the two units of knob 195 and the two units of clip 120 such that the straight line incisions of sponge 150D attach to the two units of clip 120.

Assembly 12 (A12) comprises collection device 195 operatively connected to sponge 150D, cap 180, and the tube. The tube also connects to cap 180, wherein cap 180 attaches to connector 115 of collection device 195. Sponge holder 110C, which comprises two units of knob 190, two units of rear extender 195, and two units of clips 200, is integrated into this variant of collection device 195, wherein sponge holder 110C receives sponge 150D, as depicted in FIG. 17.

Figure 19:
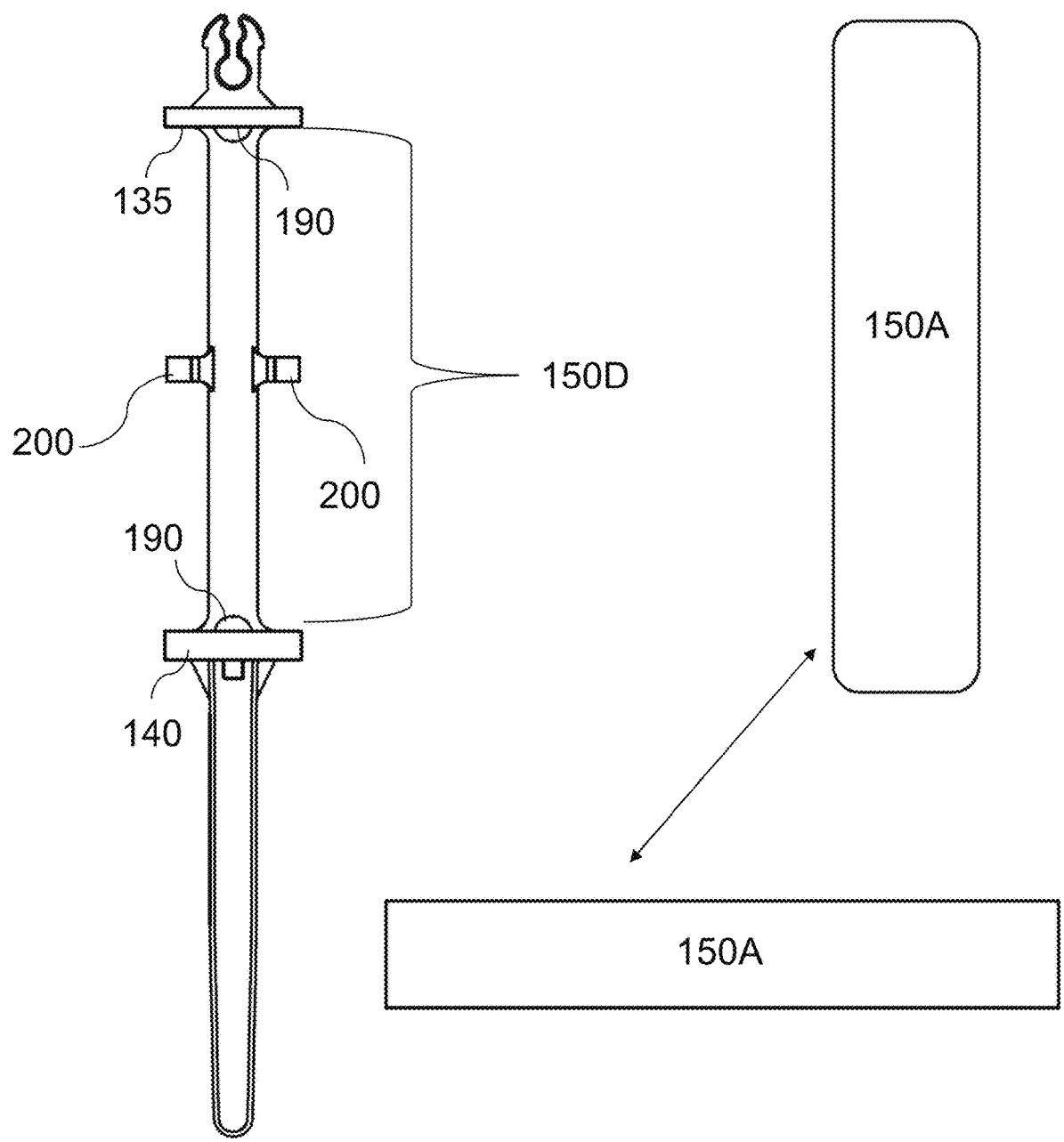
FIG. 19 is a depiction of a collection device and sponge.
Figure 20:
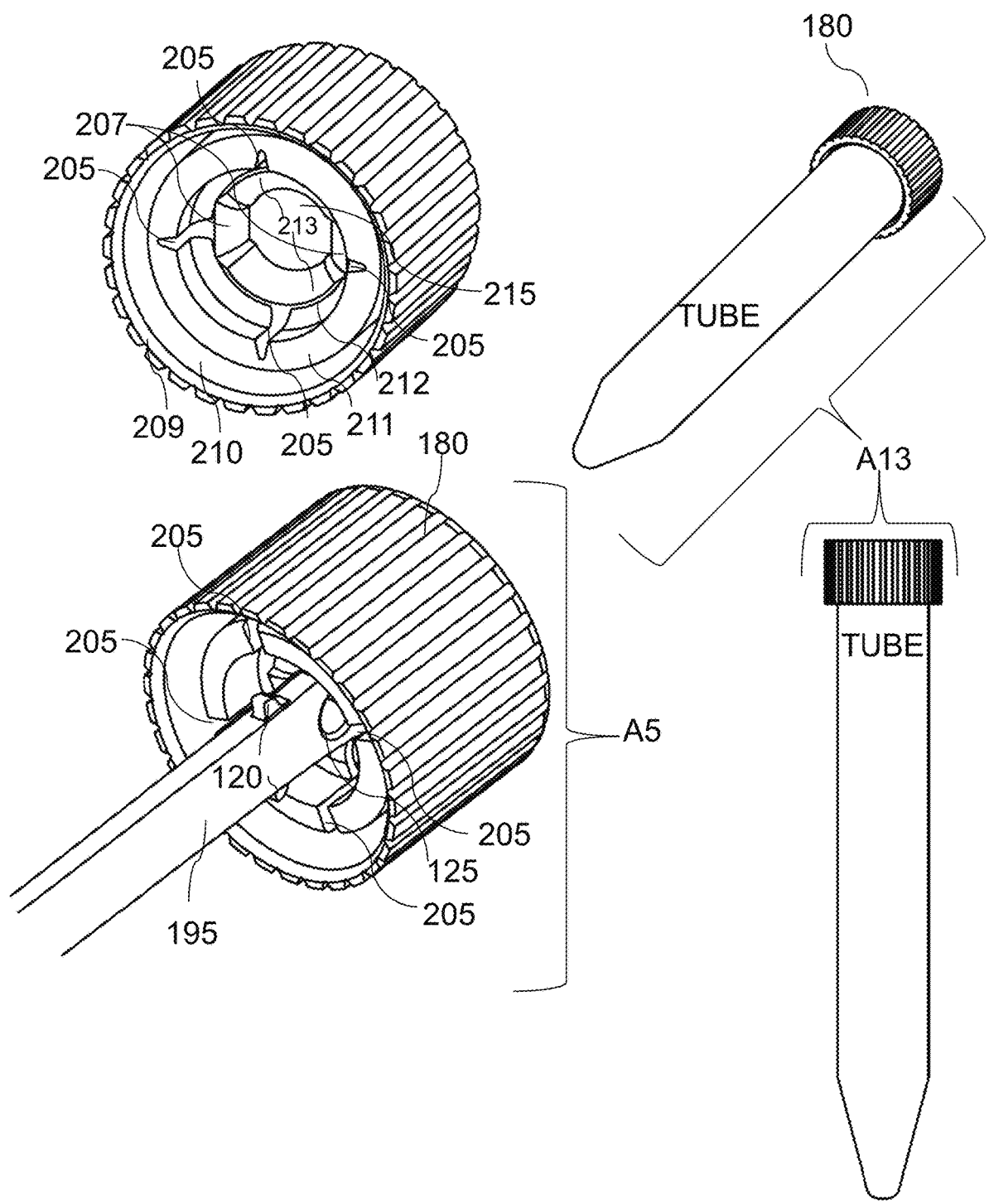
FIG. 20 is a depiction of the dimensions of a cap and tube.
Figure 21:
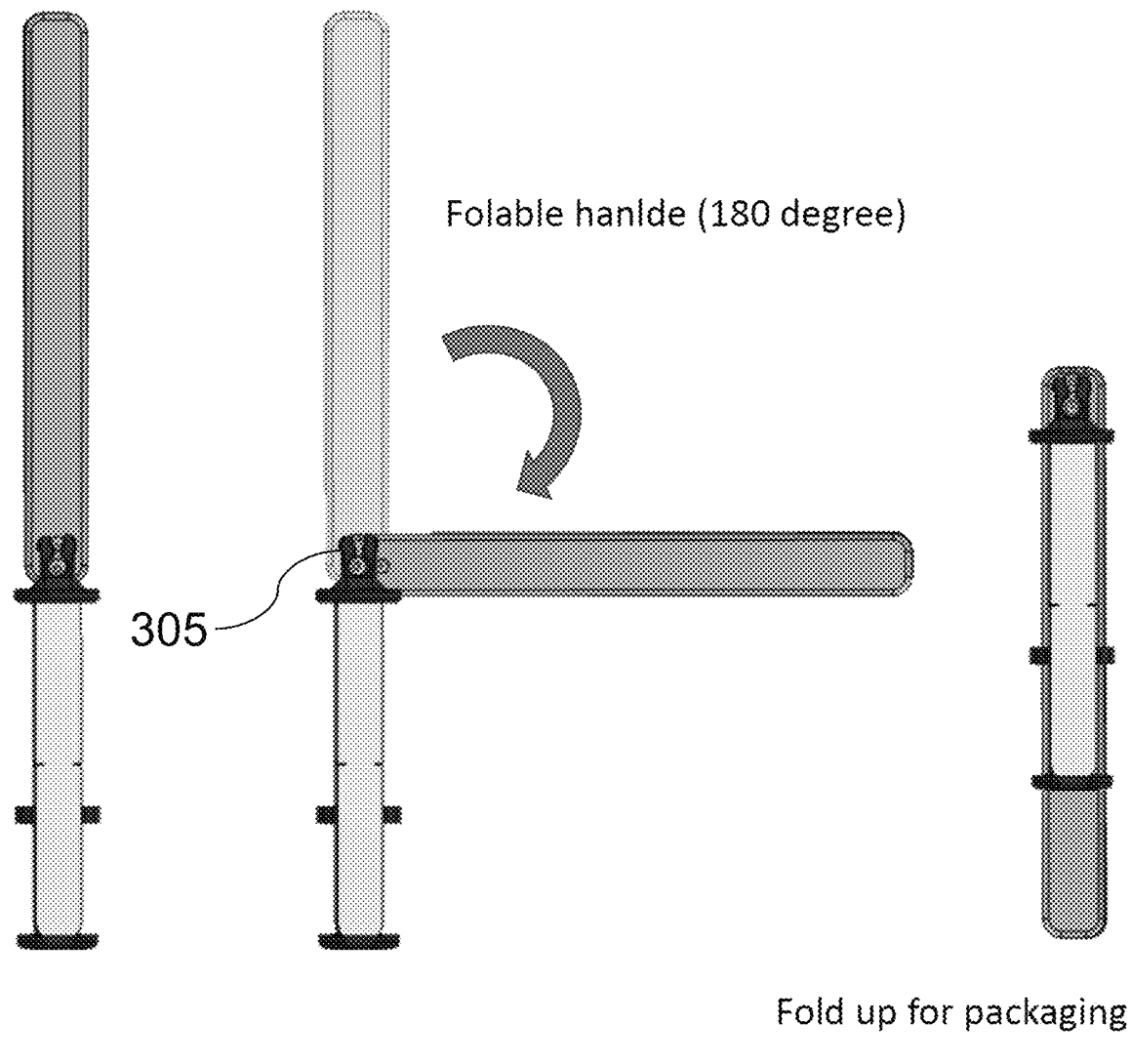
FIG. 21 illustrate a kit of the present invention, in which the clip is rotatable while joined to the collection device.
Figure 22:
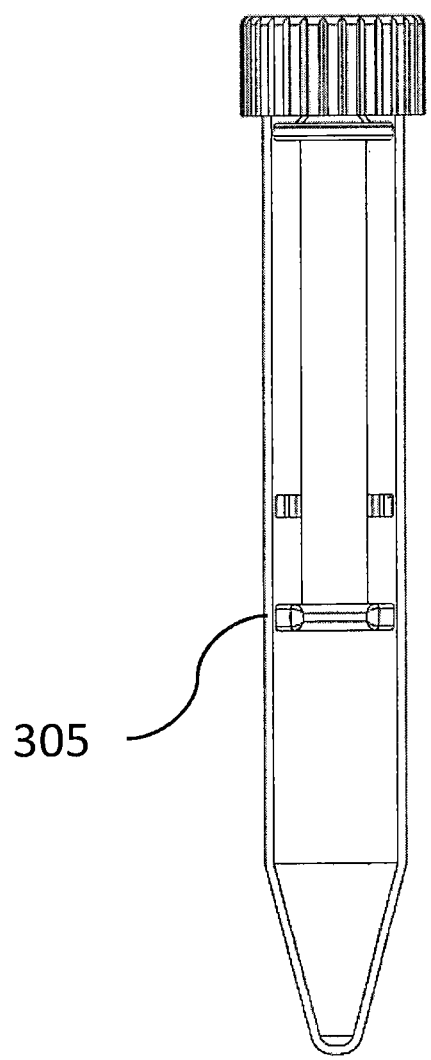
FIG. 22 illustrates the collection device inside a tube, according to some embodiments of the present invention.
Figure 23:
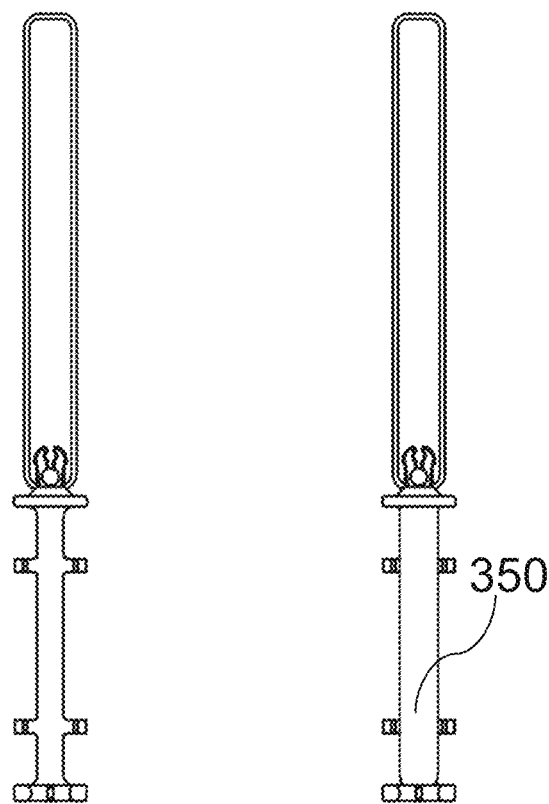
FIG. 23 illustrates a sponge held by the collection device while the clip is parallel to the collection device and above the collection device, according to some embodiments of the present invention.
Figure 24:
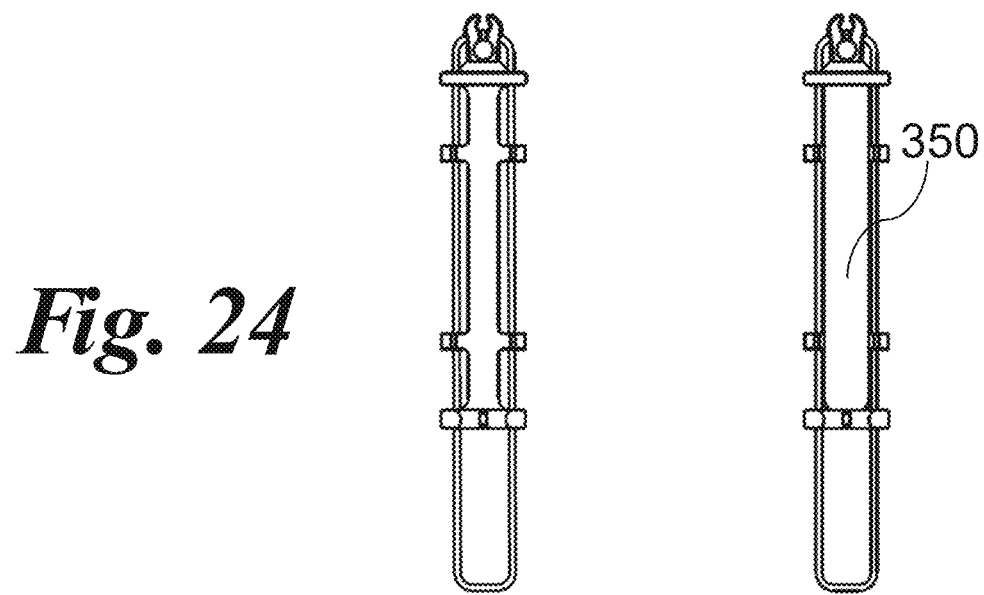
FIG. 24 illustrates a sponge held by the collection device while the clip is parallel to the collection device and behind the collection device, according to some embodiments of the present invention.
Figure 25:
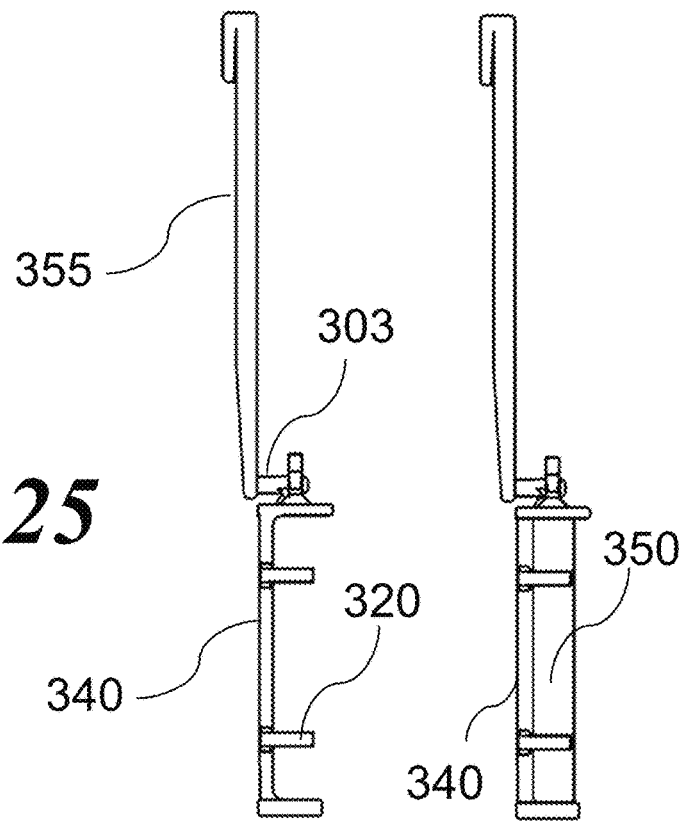
FIG. 25 illustrates a kit of the present invention, with and without the sponge from the side.

As depicted in FIG. 19, collection device 195 comprises sponge holder 110D. A unit of knob 195 is disposed on seat 140 and a unit of knob 195 is disposed on wall 135. Two units of clip 200 are disposed on the sides of sponge holder 110D. Sponge 150A is contained within the two units of knob 195 and the units of clip 200, a disposed onto sponge holder 110D. The length of sponge holder 110D is 51.80 cm, the length spanning from sponge stopper 105 to wall 135 is 103.80 cm, the length spanning from sponge stopper 105 to seat 140 is 47.00 cm, and the length spanning from sponge stopper 105 to connector 115 is 112.79 cm. As depicted in FIG. 20, the dimensions of sponge 150A are 11.26 cm by 51.80 cm by 8.24 cm.

Assembly 13 (A13) comprises cap 180 and the tube (similar to the ones above), as depicted in FIG. 20. Cap 180 may be screwed on or pressed onto the top portion of the tube to make sturdy fit. Cap 180 comprises layers 209, 210, 211, and 212. The ridges on cap 180 are disposed on layer 209, which is operatively connected to layer 210. Layer 210 is disposed in between layer 209 and layer 211. Layer 211 is disposed in between layer 210 and layer 212. Layer 212 is disposed in between layer 211 and layer 213. Layer 213 comprises two parts which are arranged such that two units of groove 207 reside within the two parts of layer 213 such that the two units of groove 207 are opposite to each other and a cavity separates the two parts of layer 213. There are four units of groove 205 spanning layers 211 and 212. The entirety of layer 211 is spanned by each unit of groove 205, whereas groove 205 spans a portion of layer 212. Two of the four units of groove 205 are operatively connected to groove 207. Two units of groove 205 are operatively connected to layer 213. As depicted in A5 in FIG. 20, cavity 125 aligns with the two units of groove 205 are operatively connected to layer 213 and extenders 125 can be received by the by the two units of groove 205 operatively connected to layer 213.

Figure 30:
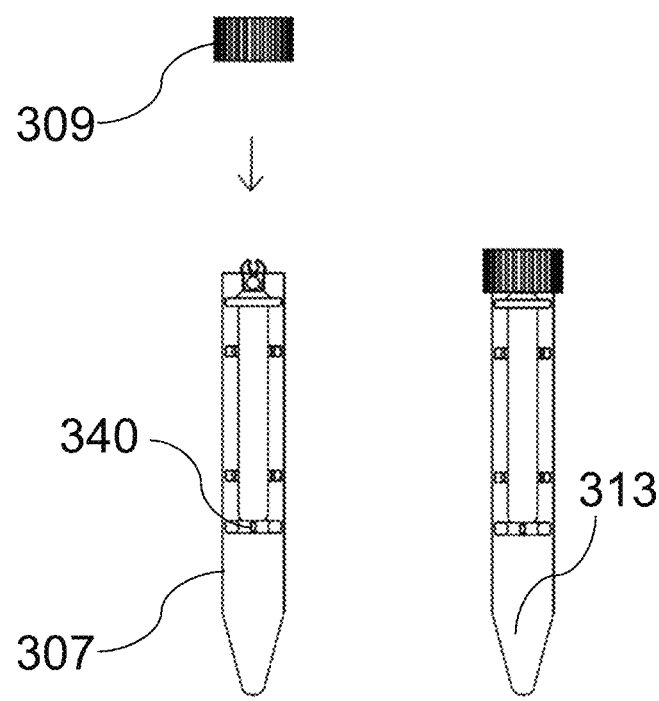
FIG. 30 illustrates the closure of the tube via a cap that connects to the collection device, according to some embodiments of the present invention.
Figure 31:
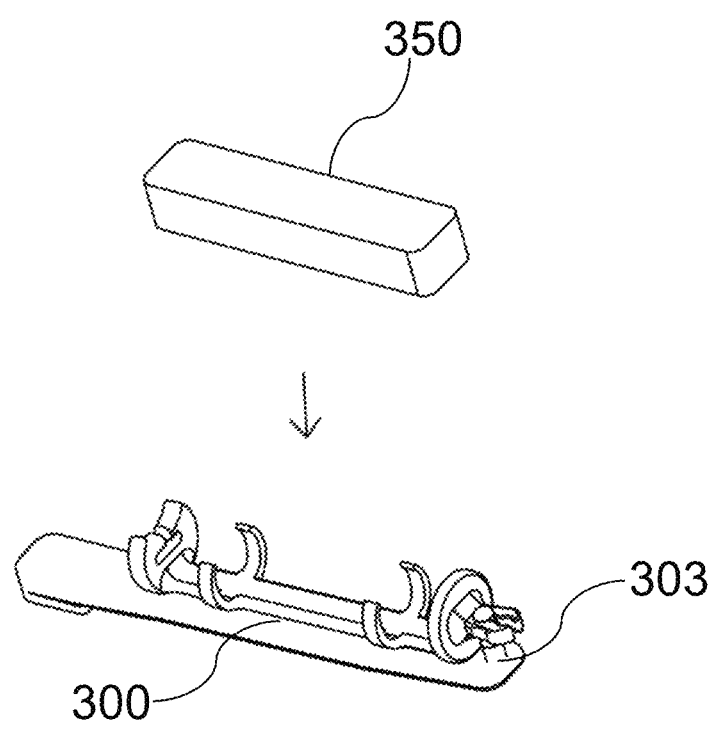
FIG. 31 illustrates the joining of a sponge into a collection device, according to some embodiments of the present invention.
Figure 32:
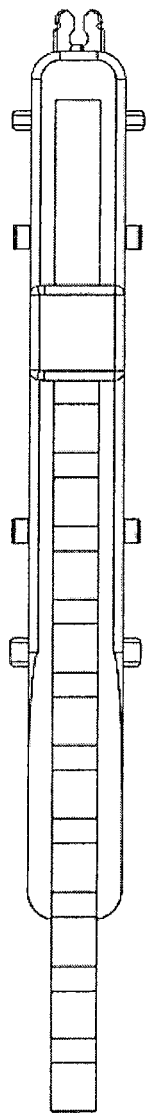
FIG. 32 illustrates a test strip joined to a clip, according to some embodiments of the present invention.

In another variant, referring to FIGS. 21-32, a cupless, sponge-mounted urine collection device 300 is provided. The device 300 has a sponge holder 310. The collection device 300 is attached to a rotatable clip 355 at a connector 315 of collection device 300 via a neck 303. The clip 355 is configured to retain a urine test strip 351. The connector 315 is configured to be received into a recess 308 of a cap 309 of a collection tube 307. The neck 303 is sized to permit the rotatable clip to rotate behind the sponge holder 310. The neck 303 and dimensions of the sponge holder 310 are sized and shaped to permit the device 300 to be inserted into collection tube 307 when the clip 355 is rotated behind directly behind the sponge holder 310. The sponge holder 300 comprises side extenders 320 and seat 340, which are arranged such that sponge 350 fits in between side extenders 320 and seat 340. The sponge holder 310 comprises wall 335 and the seat 340, which are arranged such that sponge 350 fits in between wall 335 and seat 340. In an embodiment, the seat 340 is sized and shaped, along with the tube 307, so that seat 340 becomes wedged inside tube 307 at a location that results in the connector 315 being positioned to receive into recess 308 of the cap 309 while permitting cap 308 to form a liquid tight seal with the tube 307 as shown in FIG. 30.

The cupless, sponge-mounted urine collection device 300 is provided with a urine test strip attached to the clip on a side of the clip that always faces away from the sponge. The device is configured to perform two functions: 1. First as a urinalysis strip holder for permitting urinalysis strip testing and 2. as a urine collection device for lab testing. The device is packaged in a compact state and provided to a patient, with the clip rotated behind the sponge holder as in FIGS. 24 and 31. The advantage of it being compact, it that it can be more efficiently sealed and packaged for shipment and distribution and less subject to being punctured and contaminated.

The tube 307 and device 300 are sized and shaped to permit a space 313 to form in the bottom of tube 307 below the device 300 that allows for urine collected in the sponge 350 to be centrifuged while in the tube 307 which causes the urine to collect in the space 313 and separate from the sponge 350, without the need for a urine collection cup.

Figure 33:
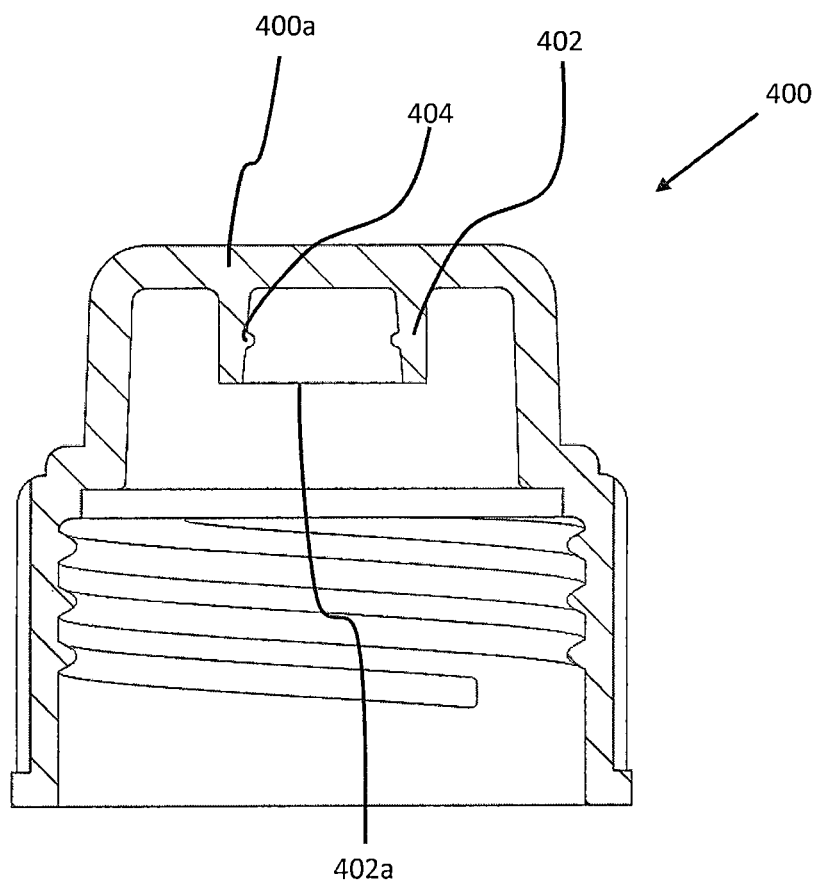
FIG. 33 illustrates a cap with a hollow cylindrical protrusion, according to some embodiments of the present invention.

Referring now to FIG. 33, in some embodiments of the present invention, the cap 400 includes a hollow cylindrical protrusion 402 extending from a bottom surface of the top of the cap 400a downward. The protrusion 402 has an open end 402a on the bottom thereof. The protrusion 402 includes a lip 404 extending radially inward at a location between the top the protrusion 402 and the bottom end 402a of the protrusion 402.

Figure 34:
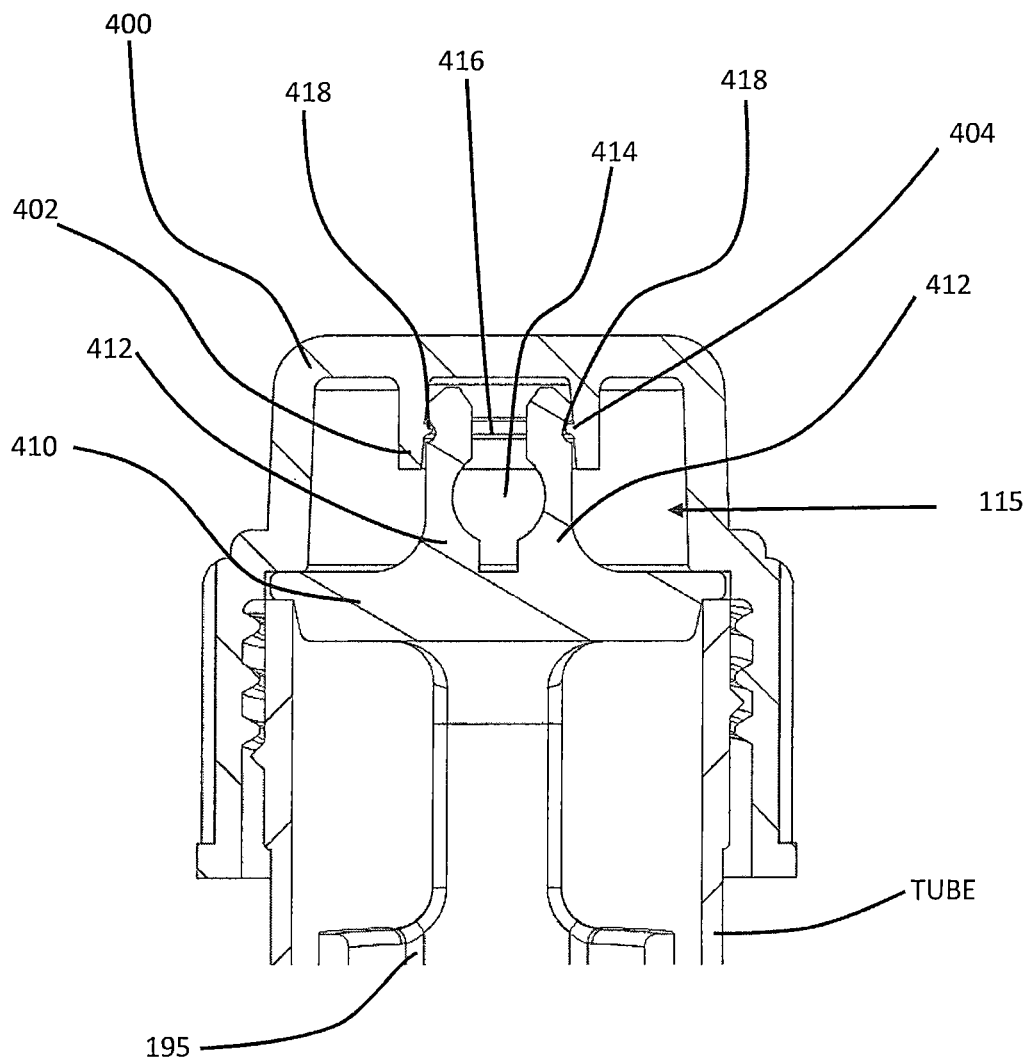
FIG. 34 illustrates a connection between a cap closing a tube and a collection device in the tube, according to some embodiments of the present invention.

As seen in FIG. 34, the connector 115 of the collection device 195 includes a lid 410 and two flexible prongs 412 extending upward from the top of the lid 410. The connector is at the top end of the collection device. The lid is sized to cover an opening of the tube and rest on the rim of the tube to prevent further insertion of the collection device in the tube. Between the two prongs 412, there are a lower cavity 414 and an upper cavity 416 above the lower cavity 416. The lower cavity 414 has a circular side cross-section and is wider than the upper cavity 416. The lower cavity 414 and the upper cavity 416 connect to each other, such that the upper cavity 416 is a narrower continuation of the upper cavity 414.

The prongs 412 includes grooves 418 on outer sides thereof. When the collection device is inserted into the tube, the lid 410 touches the rim of the tube, preventing the collection device 195 from entering the tube any further. The cap 400 closes the tube, and the prongs 412 are received by the cap's protrusion 402, such that the grooves 418 cooperate with the lip 404 of the cap's protrusion 404, to connect the collection device 195 with the cap. In this manner, when the cap 400 is removed from the tube, the collection device 195 comes out of the tube as well, due to its connection to the cap.

In some embodiments of the present invention, the inner portion of the protrusion 402 widens from the top end of the protrusion to the bottom end of the protrusion so that the inner surface of the protrusion is inclined. In this manner, as the prongs travel deeper into the protrusion 402, they bend more and more, applying pressure to the inner portion of the protrusion and strengthening the connection between the cap 400 and the collection device 195.

Figure 35:
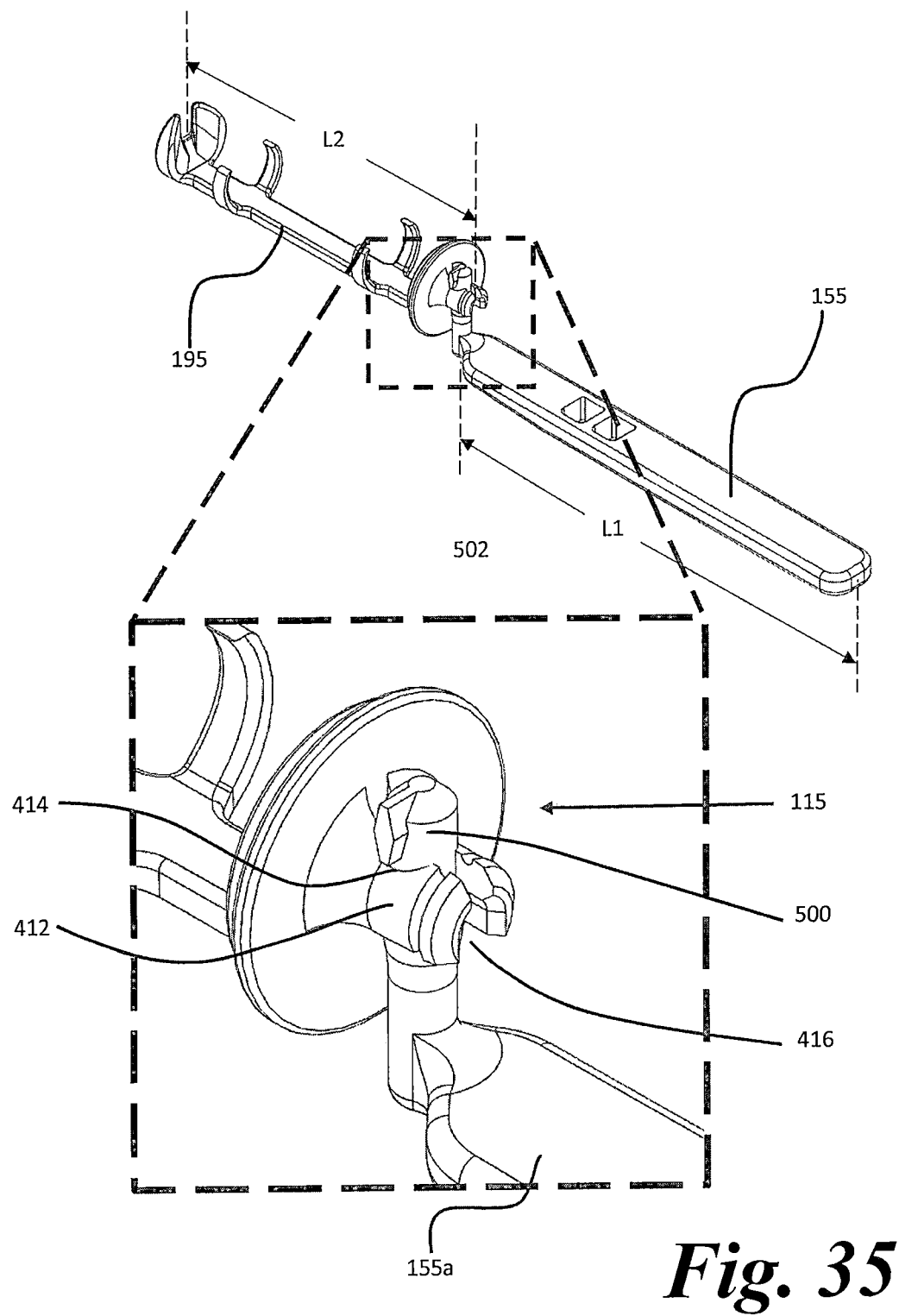
FIG. 35 illustrates a connection between a clip and a collection device, according to some embodiments of the present invention.

Referring now to FIG. 35, the clip 155 has a main body 155a which is elongated, with a longer (longitudinal) dimension L1 being substantially equal (±20%) to a longer (longitudinal) dimension L2 of the collection device 195. In this manner, the user can hold the main body 155a of the clip 155 in order to aim urine at the sponge held by the collection device 195 without soiling the user's hand that holds the clip 155. Dimension L1 may optionally be between 2 inches to 3.5 inches, or 3 inches to 4.5 inches, or 4 inches to 5 inches.

Figure 27:
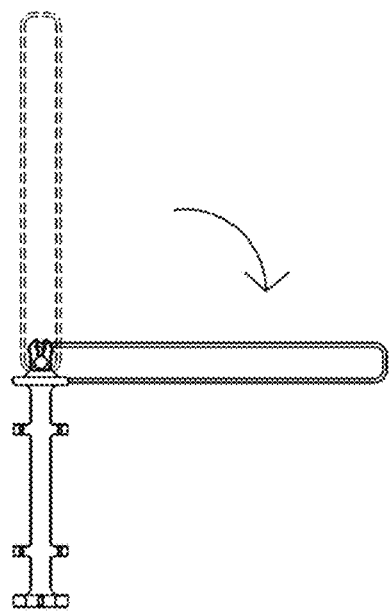
FIGS. 27 and 28 illustrates a kit of the present invention, with a rotatable clip.
Figure 28:
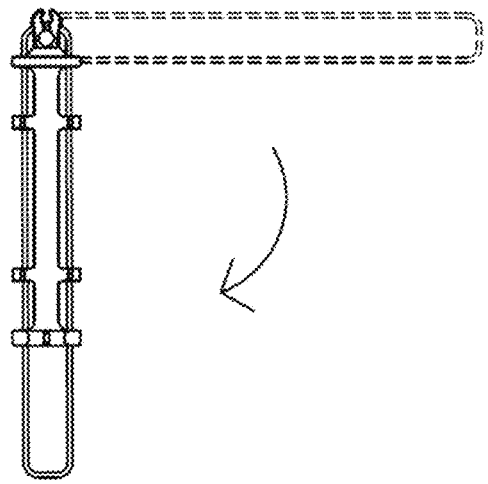
Figure 29:
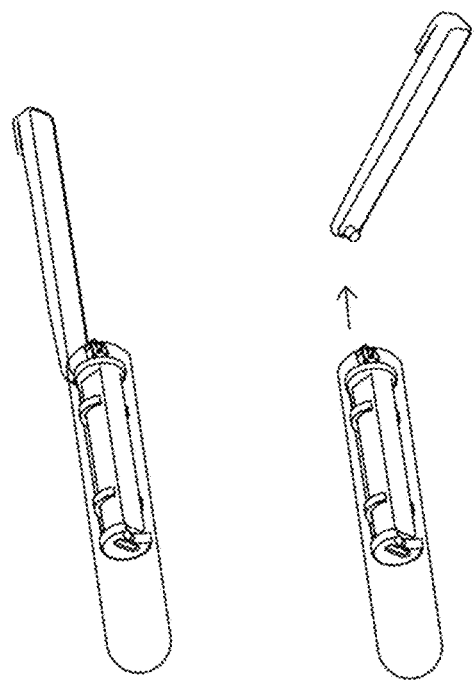
FIG. 29 illustrate the insertion of the collection device into a tube and the removal of the clip from the collection device, according to some embodiments of the present invention.

In some embodiments of the present invention, the clip 155 has an extension 500 extending perpendicularly to the longer (longitudinal) dimension L1. The extension 500 is cylindrical and is configured to be cooperate with the lower cavity 414 between the prongs 412 of the connector 115 to removably join the clip 155 to the collection device 195. Because the extension 500 is cylindrical and the lower cavity 414 has a circular cross section, the clip 155 is rotatable around the extension 500 with respect to the collection device 195 when the clip is connected to the collection device 195, as shown in FIGS. 27-28. In some embodiments the extension 500 is long enough to clear the connector 115, allowing a 360-degree rotation of the clip 155 with respect to the collection device 195, so the clip can be tucked behind the collection device 195 in a storage configuration.

In some embodiments of the present invention, the extension 500 has a flange 502 at or near the end of the extension that is farthest from the main body 155a of the clip 155. The flange 502 is perpendicular to the extension and is sized to pass through the upper cavity 416. When the longer dimension L1 of clip 155 is perpendicular to the longer dimension of the L2 of the collection device 195 such that the flange 502 is aligned with the upper cavity 416 of the connector 115, the clip 155 can be removed from the connector 115 of the collection device 195 by simply pulling the clip rearward so the extension 500 slides through the lower cavity 414 and the flange 502 slides through the upper cavity 416. In every other configuration, the flange 502 blocks the motion of the extension 500 through the lower cavity 412.

Figure 26:
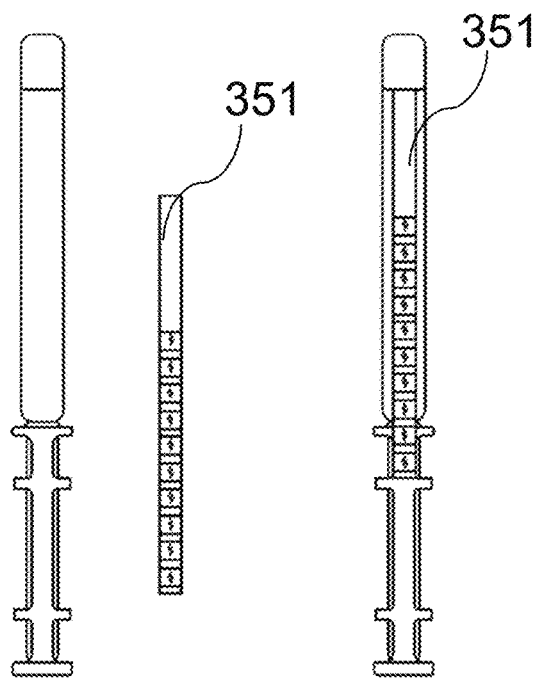
Figure 36:
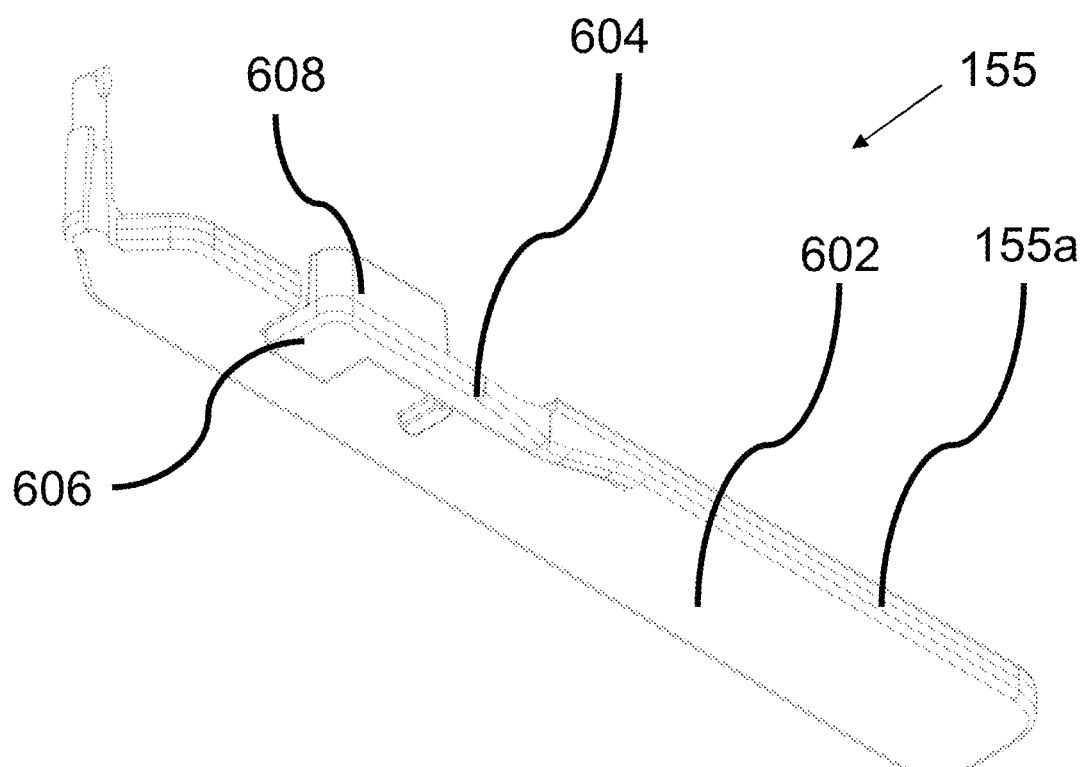
FIG. 36 is a three-quarters view of a clip of some embodiments of the present invention, showing the rear surface of the clip.
Figure 37:
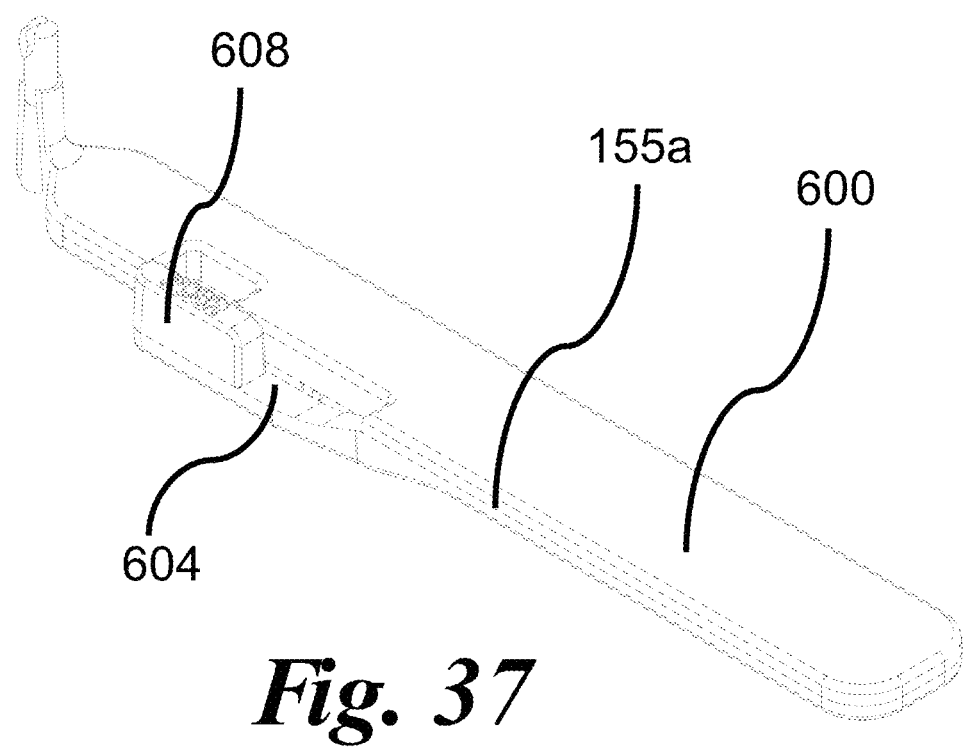
FIG. 37 is a three-quarters view of a clip of some embodiments of the present invention, showing the front surface of the clip.

Referring now to FIGS. 36 and 37, in some embodiments of the present invention, the main body 155a of the clip 155 has a planar shape which includes front surface 600 and rear surface 602. An arm 604 extends from a lateral side of the main body 155a and slopes rearward of the rear surface 602. The arm 604 has a tab 606 that extends toward the rear surface 606 and presses against the rear surface 606. When the arm 604 is moved rearward, a gap opens between the tab 606 and the rear surface 602. In this gap, a test strip 351 can be inserted, as seen in FIG. 26. As the strip is released, the gap closes and the test strip 351 is held in place between the rear surface 606 and the tab 606. Once the user has urinated on the test strip and the sponge, the arm 604 can be pushed rearward again and the main body can be tilted so that the test strip slides out of the main body 155a without touching the user or a medical professional handling the clip 155 and the collection device 195.

In some embodiments of the present invention, the arm 604 has a button 608 extending frontward and configured to be pushed from the front to the main body of the clip 155 to push the arm rearward and open the gap between the tab 606 and the rear surface 602.

Figure 38:
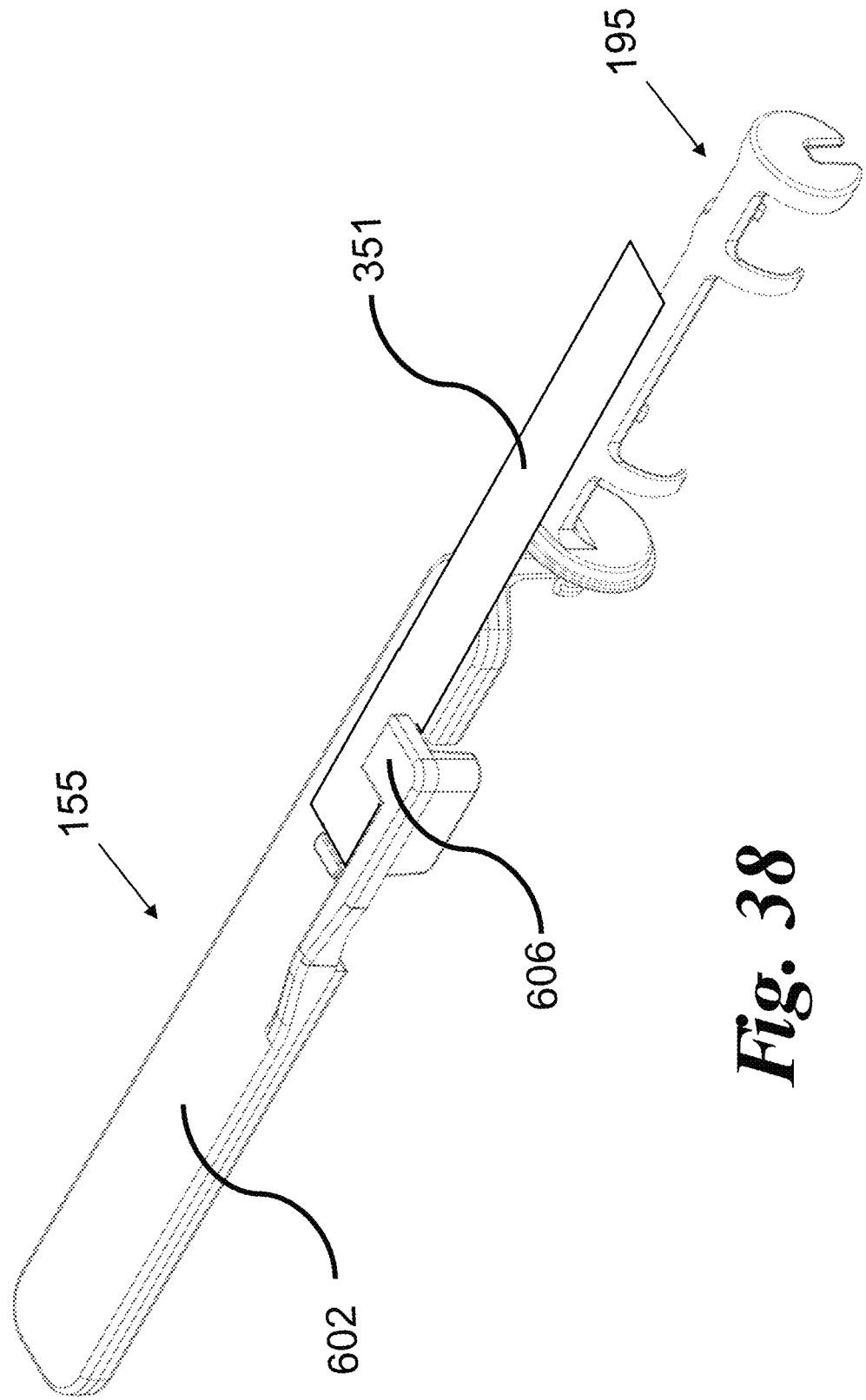
FIG. 38 illustrates a clip attached to a collection device, while a test strip is joined to the clip, according to some embodiments of the present invention.

Referring to FIG. 38, while the kit of the present invention is in use, the clip 155 is joined to the collection device 195 and the test strip 351 is held on the between the tab 606 and the rear surface 602 of the main body. A sponge (not shown) is held by the collection device 195. Holding the top of the clip 155, the user urinates on the test strip 351 and then turns the kit around to continue urinating on the sponge.

Figure 39:
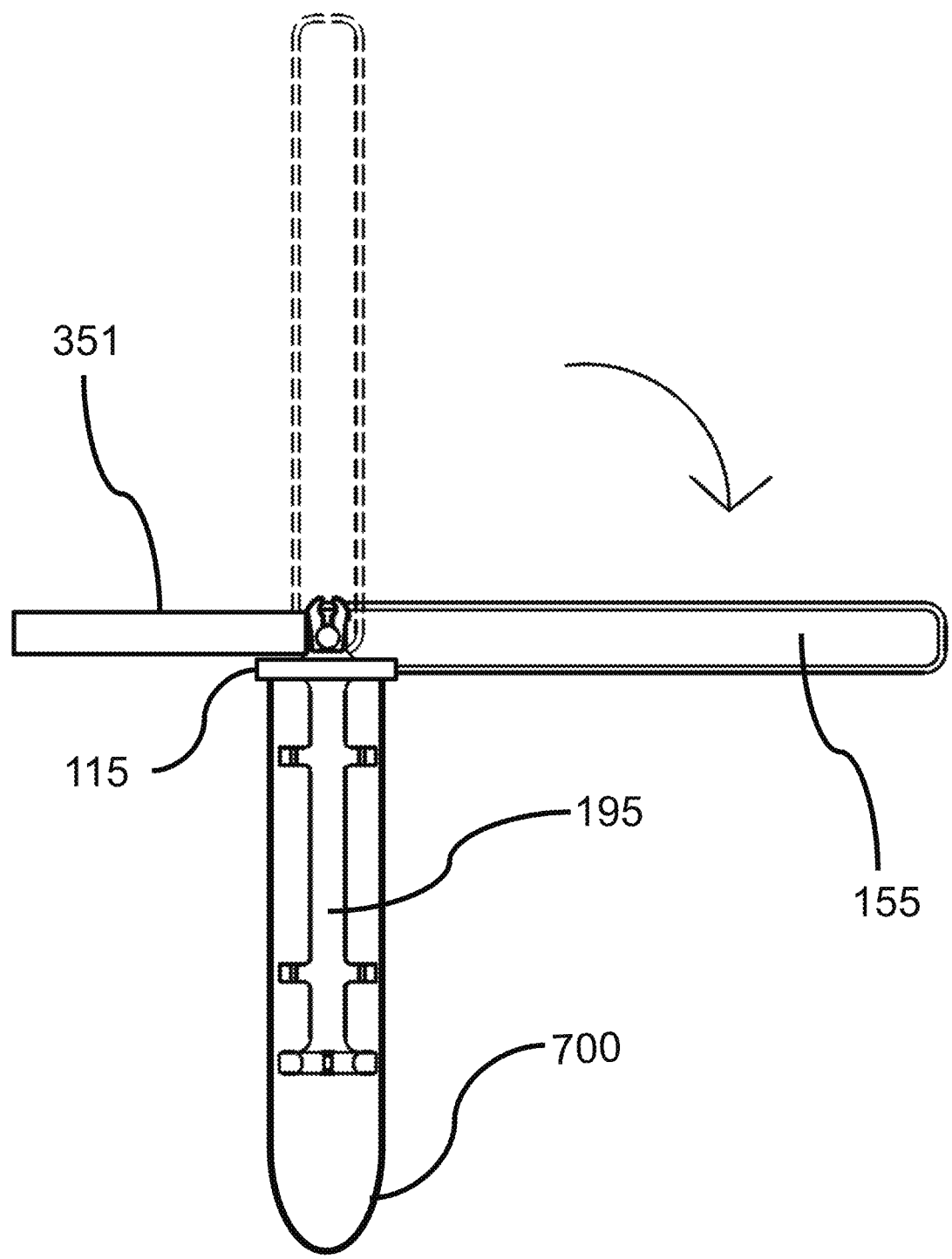
FIG. 39 illustrates the rotation of the clip with respect to the collection device in a tube prior to removal of the clip from the collection device, according to some embodiments of the present invention.
Figure 40:
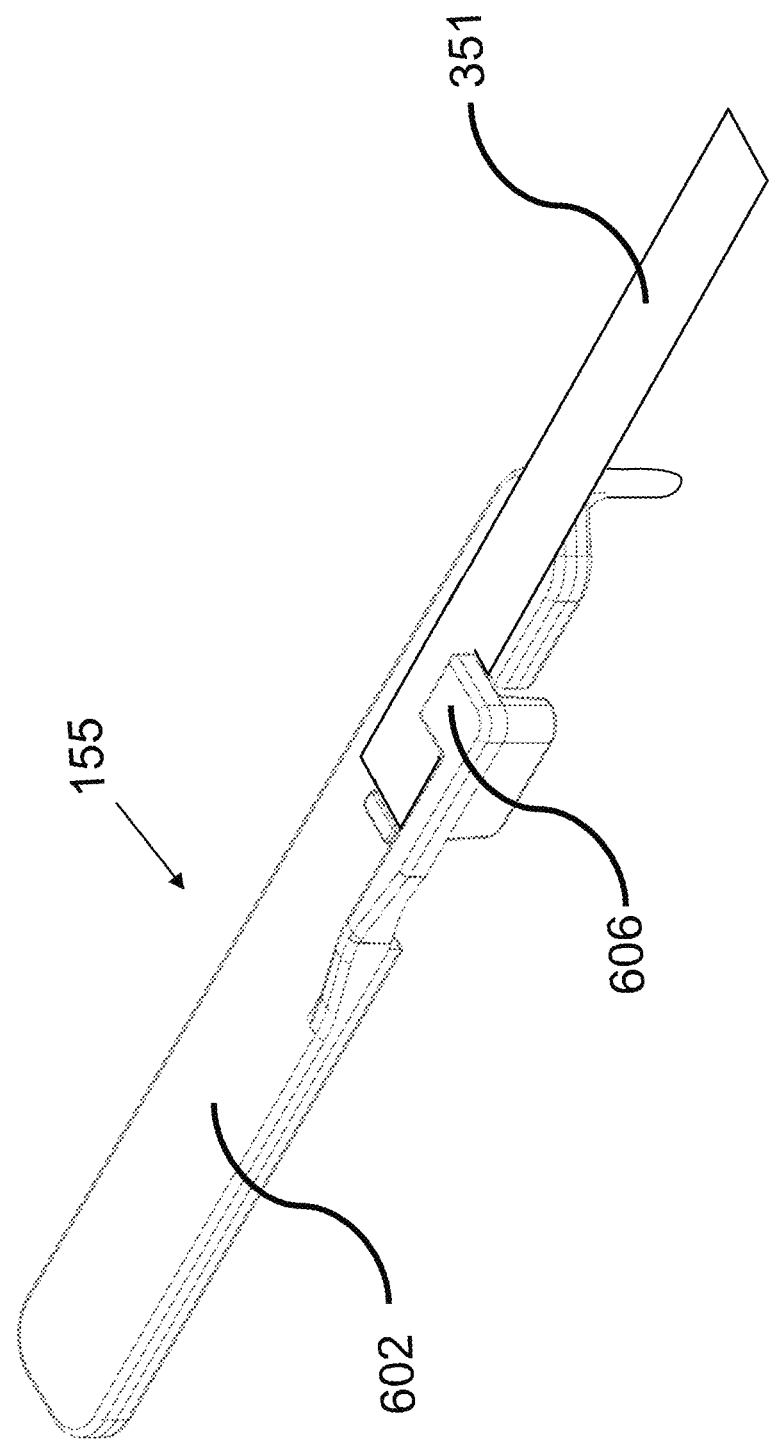
FIG. 40 illustrates a clip after separation from a collection device, with a test strip still attached to the clip, according to some embodiments of the present invention.
Figure 41:
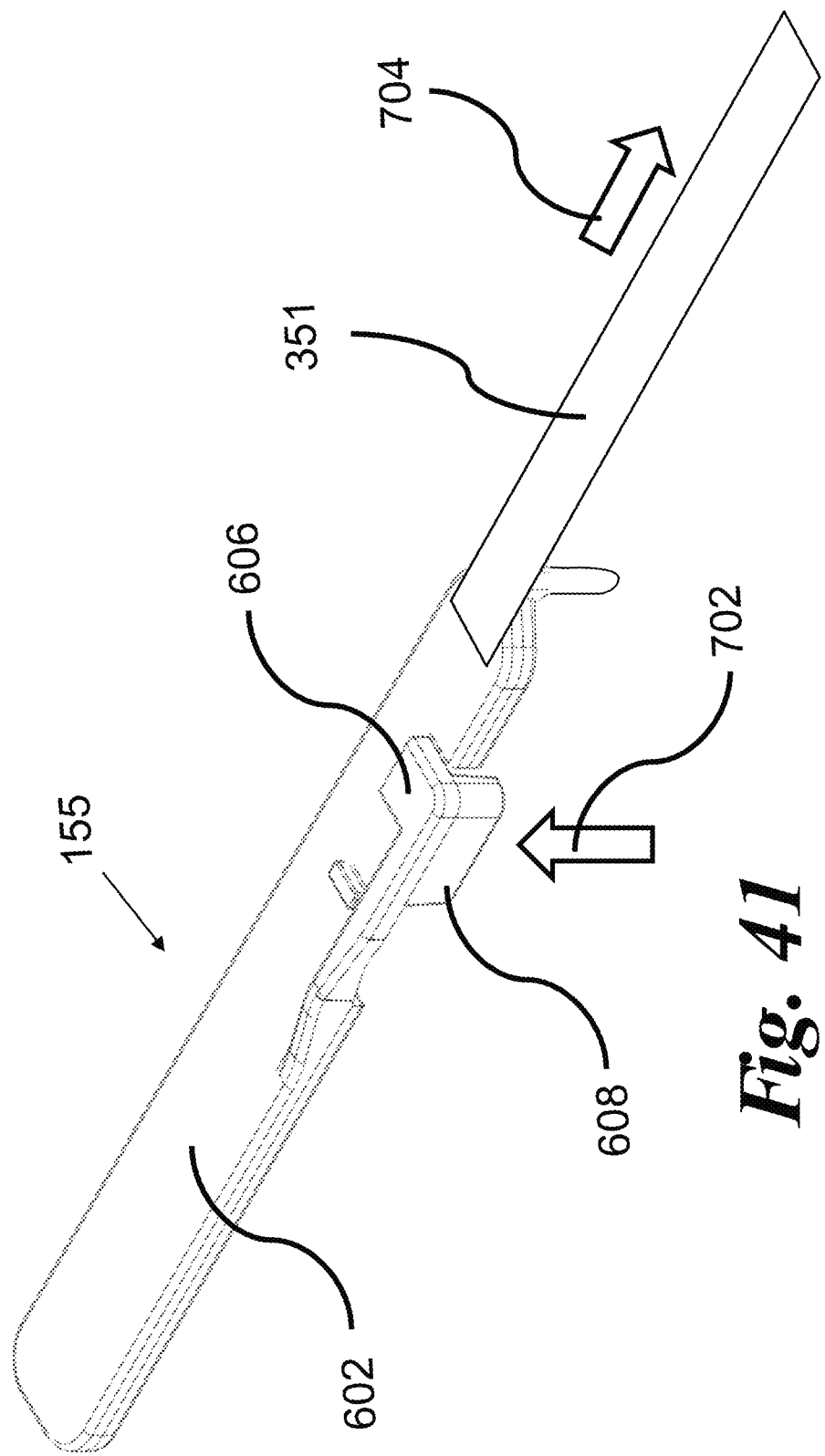
FIG. 41 illustrates a test strip sling away from the clip, according to some embodiments of the present invention.

In FIG. 39, the collection device 195 is inserted into a tube 700, such that the lid of the connector 115 contacts the rim of the tube 700 and a gap is left between the bottom of the collection device 195 and the bottom of the tube. The clip 155 is rotated so that the flange 502 (FIG. 35) is aligned with the upper gap 416 (FIG. 35). The clip 155 is removed from the collection device 195, as described above, and the tube is closed with the cap 400, as shown in FIG. 34. The tube is placed in a centrifuge by medical personnel, to remove urine from the sponge to be collected at the bottom the tube. The cap 400 is then opened and disposed of with the collection device 195 still attached to the cap 400, in order to perform tests on the urine. In FIG. 40, the test strip 351 is joined to the clip 155. In FIG. 40, the button 608 is pushed (as illustrated by arrow 702) to open the gap between the tab 606 and the rear surface 602 of the main body 155a of the clip 155. The clip 155 is tilted, to allow the test strip to slide out of the clip 155 (as illustrated by the arrow 704) onto a tray of a computer driven urinalysis reader (not shown), for examination my medical personnel. For use at home, the clip 155 serves as a holder for the urinalysis strip until the patient releases the strip from the handle to be photographed. It should be noted that during this process, the kit of the present invention decreases or eliminates contact between the urine and the user and contact between the urine and medical personnel handling the kit.

What is claimed is:

1. A kit for home urine collection and in office urine collection, comprising:
   a collector device comprising a holder portion and a connector portion, the holder portion being configured to receive a sponge;
   a clip comprising an elongated main body and an extension extending perpendicularly to a longitudinal dimension of the main body, the extension being configured to cooperate with the holder portion to removably join the clip to the collector device,
   wherein:
   the connector portion comprises a lid and two flexible prongs extending upward from the top of the lid;
   the prongs are disposed so that a lower cavity and an upper cavity are located between the prongs and are connected to each other;
   the lower cavity has a circular side-cross section and is wider than the upper cavity.

2. The kit of claim 1, wherein the extension is cylindrical and configured to be inserted in the lower cavity to join the clip to the collection device, such that clip is rotatable around the extension with respect to the collection device, when the clip is connected to the collection device.

3. The kit of claim 2, wherein the extension clears the connector portion of the collection device to enable rotation of 360 degrees of the clip around the extension with respect to the collection device, when the clip is connected to the collection device.

4. The kit of claim 1, comprising a flange at or near an end of the extension that is farthest from the main body, wherein the flange is perpendicular to the extension and sized to pass through the upper cavity.

5. The kit of claim 1, comprising a cap configured to cooperate with the connector portion to of the collector device, to join the cap and the collector device when the cap closes a tube in which the collector device is placed, wherein:
   the cap comprises a hollow cylindrical protrusion extending from a bottom surface of a top of the cap downward, the hollow cylindrical protrusion having an open bottom end;
   the hollow cylindrical protrusion comprises a lip extending radially inward between a top and a bottom end of the hollow cylindrical protrusion;
   the flexible prongs comprise grooves on outer sides thereof, such that the prongs are received in the hollow cylindrical protrusion of the cap when the cap closes the tube, and the grooves cooperate with the lip of the hollow cylindrical protrusion to connect the collection device to the cap.

6. The kit of claim 5, wherein an inner portion of the hollow cylindrical protrusion widens from the top to the bottom end of the hollow cylindrical protrusion.

7. The kit of claim 1, wherein the longitudinal dimension of the main body is substantially equal to a longitudinal dimension of the collector device.

8. A kit for home urine collection and in office urine collection, comprising:
   a collector device comprising a holder portion and a connector portion, the holder portion being configured to receive a sponge;
   a clip comprising an elongated main body and an extension extending perpendicularly to a longitudinal dimension of the main body, the extension being configured to cooperate with the holder portion to removably join the clip to the collector device, wherein:
   the main body has a planar shape and includes a front surface and a rear surface;
   the main body comprises an arm extending from a lateral side of the main body and sloping rearward of the rear surface;
   the arm comprises a tab that extends toward the rear surface and presses against the rear surface;
   the arm is movable rearward to open a gap between the tab and the rear surface for insertion of a test strip in the gap;
   when the arm is released, the arm is configured for closing the gap to hold the test strip between the tab and the rear surface.

9. A kit for home urine collection and in office urine collection, comprising:
   a sponge for absorbing urine when urinated upon;
   a collector device comprising a holder portion and a connector portion, the holder portion being configured to receive the sponge;
   a clip comprising an elongated main body and an extension extending perpendicularly to a longitudinal dimension of the main body, the extension being configured to cooperate with the holder portion to removably join the clip to the collector device;
   a tube configured to receive the collector device
   a cap configured to cooperate with the connector portion to of the collector device, to join the cap and the collector device when the cap closes the tube in which the collector device is placed;

a test strip, comprising distinct chemical pads with respective reagents that change color upon physical exposure to urine depending on presence of entities in the urine;

wherein:
- the main body has a planar shape and includes a front surface and a rear surface;
- the main body comprises an arm extending from a lateral side of the main body and sloping rearward of the rear surface;
- the arm comprises a tab that extends toward the rear surface and presses against the rear surface;
- the arm is movable rearward to open a gap between the tab and the rear surface for insertion of the test strip in the gap;
- when the arm is released, the arm is configured for closing the gap to hold the test strip between the tab and the rear surface.

* * * * *